United States Patent
Moreira Ridsdale et al.

(10) Patent No.: US 12,185,974 B2
(45) Date of Patent: Jan. 7, 2025

(54) SURGICAL TOOL WITH NESTED SHAFT TUBES

(71) Applicant: Intuitive Surgical Operations, Inc., Sunnyvale, CA (US)

(72) Inventors: David I. Moreira Ridsdale, Saratoga, CA (US); Harsukhdeep S. Ratia, Los Altos Hills, CA (US); Craig Tsuji, San Jose, CA (US); Zhou Ye, Santa Clara, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 31 days.

(21) Appl. No.: 17/768,298

(22) PCT Filed: Oct. 15, 2020

(86) PCT No.: PCT/US2020/055794
§ 371 (c)(1),
(2) Date: Apr. 12, 2022

(87) PCT Pub. No.: WO2021/076765
PCT Pub. Date: Apr. 22, 2021

(65) Prior Publication Data
US 2024/0148405 A1 May 9, 2024

Related U.S. Application Data

(60) Provisional application No. 62/916,712, filed on Oct. 17, 2019, provisional application No. 62/916,716, filed on Oct. 17, 2019.

(51) Int. Cl.
| | | |
|---|---|---|
| A61B 17/34 | (2006.01) | |
| A61B 17/00 | (2006.01) | |
| A61B 90/00 | (2016.01) | |

(52) U.S. Cl.
CPC .... *A61B 17/3415* (2013.01); *A61B 17/00234* (2013.01); *A61B 2017/00477* (2013.01); *A61B 17/3474* (2013.01); *A61B 2090/064* (2016.02)

(58) Field of Classification Search
CPC .......... A61B 17/3415; A61B 17/00234; A61B 17/3474; A61B 2017/00477;
(Continued)

(56) References Cited

U.S. PATENT DOCUMENTS

| | | |
|---|---|---|
| 3,325,761 A | 6/1967 | Mclellan |
| 3,358,511 A | 12/1967 | Bargen |

(Continued)

FOREIGN PATENT DOCUMENTS

| | | |
|---|---|---|
| CN | 103717355 A | 4/2014 |
| CN | 105682597 A | 6/2016 |

(Continued)

OTHER PUBLICATIONS

International Search Report and Written Opinion for Application No. PCT/US2020/055794, mailed Mar. 16, 2021, 14 pages.
(Continued)

*Primary Examiner* — Amanda K Hulbert
*Assistant Examiner* — Natasha Patel

(57) ABSTRACT

A surgical instrument includes a chassis, an outer tube having a proximal end operably coupled to the chassis, and an inner tube extending within the outer tube. The inner tube has a proximal end operably coupled to the chassis to allow slidable movement of the inner tube relative to the outer tube in response to a force imparted to a distal end of the inner tube, and such that frictional force imparted to an outer surface of the outer tube is not imparted to the inner member.

20 Claims, 18 Drawing Sheets

(58) Field of Classification Search
CPC ........ A61B 2090/064; A61B 2217/007; A61B 17/29; A61B 2034/301; A61B 34/30
See application file for complete search history.

(56) References Cited

U.S. PATENT DOCUMENTS

| | | | |
|---|---|---|---|
| 4,064,758 A | 12/1977 | Harrison |
| 4,146,864 A | 3/1979 | Bethe |
| 4,507,170 A | 3/1985 | Myhre |
| 4,525,220 A | 6/1985 | Sasa et al. |
| 4,589,403 A | 5/1986 | Ouchi et al. |
| 5,024,107 A | 6/1991 | Bethe |
| 5,108,060 A | 4/1992 | Beele |
| 5,251,611 A | 10/1993 | Zehel et al. |
| 5,333,504 A | 8/1994 | Lutz et al. |
| 5,792,135 A | 8/1998 | Madhani et al. |
| 5,795,404 A | 8/1998 | Murphy et al. |
| 5,855,583 A | 1/1999 | Wang et al. |
| 6,005,199 A | 12/1999 | Harada et al. |
| 6,197,017 B1 | 3/2001 | Brock et al. |
| 6,206,903 B1 | 3/2001 | Ramans |
| 6,394,998 B1 | 5/2002 | Wallace et al. |
| 6,459,926 B1 | 10/2002 | Nowlin et al. |
| 6,494,882 B1 | 12/2002 | Lebouitz et al. |
| 6,594,552 B1 | 7/2003 | Nowlin et al. |
| 6,663,641 B1 | 12/2003 | Kovac et al. |
| 6,817,974 B2 | 11/2004 | Cooper et al. |
| 6,994,708 B2 | 2/2006 | Manzo |
| 7,083,571 B2 | 8/2006 | Wang et al. |
| 7,090,683 B2 | 8/2006 | Brock et al. |
| 7,169,141 B2 | 1/2007 | Brock et al. |
| 7,935,130 B2 | 5/2011 | Williams |
| 7,947,000 B2 | 5/2011 | Vargas et al. |
| 8,075,476 B2 | 12/2011 | Vargas |
| 8,152,756 B2 | 4/2012 | Webster et al. |
| 8,157,744 B2 | 4/2012 | Joergensen et al. |
| 8,241,271 B2 | 8/2012 | Millman et al. |
| 8,256,306 B1 | 9/2012 | Bauer et al. |
| 8,298,161 B2 | 10/2012 | Vargas |
| 8,444,631 B2 | 5/2013 | Yeung et al. |
| 8,479,969 B2 | 7/2013 | Shelton, IV |
| 8,506,555 B2 | 8/2013 | Ruiz Morales |
| 8,551,115 B2 | 10/2013 | Steger et al. |
| 8,597,280 B2 | 12/2013 | Cooper et al. |
| 8,602,288 B2 | 12/2013 | Shelton, IV et al. |
| 8,620,473 B2 | 12/2013 | Diolaiti et al. |
| 8,628,518 B2 | 1/2014 | Blumenkranz et al. |
| 8,715,226 B2 | 5/2014 | Webster et al. |
| 8,771,270 B2 | 7/2014 | Burbank |
| 8,800,838 B2 | 8/2014 | Shelton, IV |
| 8,945,095 B2 | 2/2015 | Blumenkranz et al. |
| 8,992,565 B2 | 3/2015 | Brisson et al. |
| 9,028,494 B2 | 5/2015 | Shelton, IV et al. |
| 9,192,448 B2 | 11/2015 | Blumenkranz |
| 9,204,923 B2 | 12/2015 | Manzo et al. |
| 9,232,979 B2 | 1/2016 | Parihar et al. |
| 9,533,122 B2 | 1/2017 | Weitzner et al. |
| 9,707,684 B2 | 7/2017 | Ruiz et al. |
| 9,782,214 B2 | 10/2017 | Houser et al. |
| 9,883,920 B2 | 2/2018 | Blumenkranz et al. |
| 9,952,107 B2 | 4/2018 | Blumenkranz et al. |
| 10,085,809 B2 | 10/2018 | Blumenkranz et al. |
| 10,130,366 B2 | 11/2018 | Shelton, IV et al. |
| 10,201,365 B2 | 2/2019 | Boudreaux et al. |
| 10,219,874 B2 | 3/2019 | Yu et al. |
| 10,238,458 B2 | 3/2019 | Verner et al. |
| 10,398,433 B2 | 9/2019 | Boudreaux et al. |
| 10,653,435 B2 | 5/2020 | Shelton, IV et al. |
| 10,682,141 B2 | 6/2020 | Moore et al. |
| 10,881,280 B2 | 1/2021 | Baez, Jr. |
| 11,000,345 B2 | 5/2021 | Lambrecht et al. |
| 11,020,112 B2 | 6/2021 | Shelton, IV et al. |
| 11,045,270 B2 | 6/2021 | Shelton, IV et al. |
| 11,135,398 B2 | 10/2021 | Tilson et al. |
| 2002/0029013 A1 | 3/2002 | Paskar |
| 2002/0087048 A1 | 7/2002 | Brock et al. |
| 2003/0109852 A1 | 6/2003 | Peterson et al. |
| 2004/0015151 A1 | 1/2004 | Chambers |
| 2005/0065403 A1 | 3/2005 | Takase et al. |
| 2005/0154379 A1 | 7/2005 | McGowan, Sr. et al. |
| 2007/0005002 A1 | 1/2007 | Millman et al. |
| 2007/0043338 A1 | 2/2007 | Moll et al. |
| 2007/0078484 A1 | 4/2007 | Talarico et al. |
| 2007/0100206 A1 | 5/2007 | Lin et al. |
| 2007/0119274 A1 | 5/2007 | Devengenzo et al. |
| 2007/0137371 A1 | 6/2007 | Devengenzo et al. |
| 2007/0156019 A1 | 7/2007 | Larkin et al. |
| 2008/0009838 A1 | 1/2008 | Schena et al. |
| 2008/0046122 A1 | 2/2008 | Manzo et al. |
| 2008/0065105 A1 | 3/2008 | Larkin et al. |
| 2008/0132893 A1 | 6/2008 | D'Amelio et al. |
| 2008/0221391 A1 | 9/2008 | Weitzner et al. |
| 2008/0271270 A1 | 11/2008 | Sawada et al. |
| 2009/0031842 A1 | 2/2009 | Kawai et al. |
| 2009/0088774 A1 | 4/2009 | Swarup et al. |
| 2010/0063478 A1 | 3/2010 | Selkee |
| 2010/0219388 A1 | 9/2010 | Schena |
| 2010/0313679 A1 | 12/2010 | Larkin et al. |
| 2011/0071543 A1 | 3/2011 | Prisco et al. |
| 2011/0277775 A1 | 11/2011 | Holop et al. |
| 2011/0282356 A1 | 11/2011 | Solomon et al. |
| 2011/0295269 A1 | 12/2011 | Swensgard et al. |
| 2011/0295270 A1 | 12/2011 | Giordano et al. |
| 2012/0123441 A1 | 5/2012 | Au et al. |
| 2013/0291654 A1 | 11/2013 | Blumenkranz et al. |
| 2014/0005662 A1 | 1/2014 | Shelton, IV |
| 2014/0005678 A1 | 1/2014 | Shelton, IV et al. |
| 2014/0005708 A1 | 1/2014 | Shelton, IV |
| 2014/0238174 A1 | 8/2014 | Ikebe |
| 2014/0257333 A1 | 9/2014 | Blumenkranz |
| 2015/0051034 A1 | 2/2015 | Cooper et al. |
| 2015/0150635 A1 | 6/2015 | Kilroy et al. |
| 2015/0280384 A1 | 10/2015 | Leimbach et al. |
| 2015/0359599 A1 | 12/2015 | Fagan et al. |
| 2016/0193012 A1 | 7/2016 | Anderson et al. |
| 2016/0346513 A1* | 12/2016 | Swaney ............ A61M 25/0138 |
| 2016/0361128 A1* | 12/2016 | Seeber .................. A61B 34/30 |
| 2017/0007345 A1 | 1/2017 | Smith et al. |
| 2017/0165017 A1 | 6/2017 | Chaplin et al. |
| 2017/0172509 A1 | 6/2017 | Hein et al. |
| 2017/0172687 A1 | 6/2017 | Smith et al. |
| 2017/0215944 A1 | 8/2017 | Keffeler |
| 2018/0042689 A1 | 2/2018 | Mozdzierz et al. |
| 2018/0078249 A1 | 3/2018 | Stoy et al. |
| 2018/0116760 A1 | 5/2018 | Blumenkranz |
| 2018/0229021 A1 | 8/2018 | Donlon et al. |
| 2018/0271354 A1 | 9/2018 | Tilson et al. |
| 2019/0069966 A1* | 3/2019 | Petersen ................ A61B 90/06 |
| 2019/0094084 A1 | 3/2019 | Swinehart et al. |
| 2019/0125354 A1 | 5/2019 | Deck et al. |
| 2019/0125468 A1 | 5/2019 | Adams |
| 2019/0175188 A1* | 6/2019 | P V R .................... A61B 34/35 |
| 2019/0201018 A1 | 7/2019 | Shelton, IV et al. |
| 2019/0223960 A1 | 7/2019 | Chaplin et al. |
| 2019/0231451 A1 | 8/2019 | Lambrecht et al. |
| 2019/0231464 A1 | 8/2019 | Wixey et al. |
| 2019/0239965 A1 | 8/2019 | Abbott |
| 2019/0249759 A1 | 8/2019 | Abbott |
| 2019/0336228 A1 | 11/2019 | Blumenkranz et al. |
| 2020/0278265 A1 | 9/2020 | Suresh |
| 2020/0405375 A1 | 12/2020 | Shelton, IV et al. |
| 2021/0033478 A1 | 2/2021 | Shang |
| 2021/0045819 A1 | 2/2021 | Castillo et al. |
| 2021/0353352 A1 | 11/2021 | Petersen |
| 2021/0401524 A1 | 12/2021 | Suresh et al. |
| 2022/0003615 A1 | 1/2022 | Kadokura |
| 2023/0003596 A1 | 1/2023 | Petersen |
| 2023/0363849 A1 | 11/2023 | Comenencia et al. |
| 2024/0090959 A1 | 3/2024 | Deyanov |

FOREIGN PATENT DOCUMENTS

| | | |
|---|---|---|
| EP | 0339799 B1 | 10/1994 |
| EP | 1459692 A1 | 9/2004 |

(56) References Cited

FOREIGN PATENT DOCUMENTS

| | | |
|---|---|---|
| EP | 2362285 A2 | 8/2011 |
| EP | 2431000 A2 | 3/2012 |
| EP | 2736680 A2 | 6/2014 |
| JP | 2000172355 A | 6/2000 |
| KR | 100778387 B1 | 11/2007 |
| WO | WO-2012166806 A1 | 12/2012 |
| WO | WO-2015069887 A1 | 5/2015 |
| WO | WO-2017064303 A1 | 4/2017 |
| WO | WO-2017136332 A1 | 8/2017 |
| WO | WO-2018077527 A1 | 5/2018 |
| WO | WO-2019099562 A1 | 5/2019 |
| WO | WO-2019222004 A1 | 11/2019 |
| WO | WO-2020102774 A1 | 5/2020 |
| WO | WO-2020102776 A1 | 5/2020 |
| WO | WO-2020102778 A1 | 5/2020 |
| WO | WO-2020102780 A1 | 5/2020 |
| WO | WO-2020214221 A1 | 10/2020 |
| WO | WO-2021055276 A1 | 3/2021 |
| WO | WO-2021219396 A1 | 11/2021 |
| WO | WO-2022056213 A1 | 3/2022 |
| WO | WO-2022132885 A1 | 6/2022 |

OTHER PUBLICATIONS

Invitation to Pay Additional Fees, Communication Relating to the Results of the Partial International Search mailed on Jan. 22, 2021 for PCT Application No. PCT/US2020/055794 filed on Oct. 15, 2020, 9 pages.

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

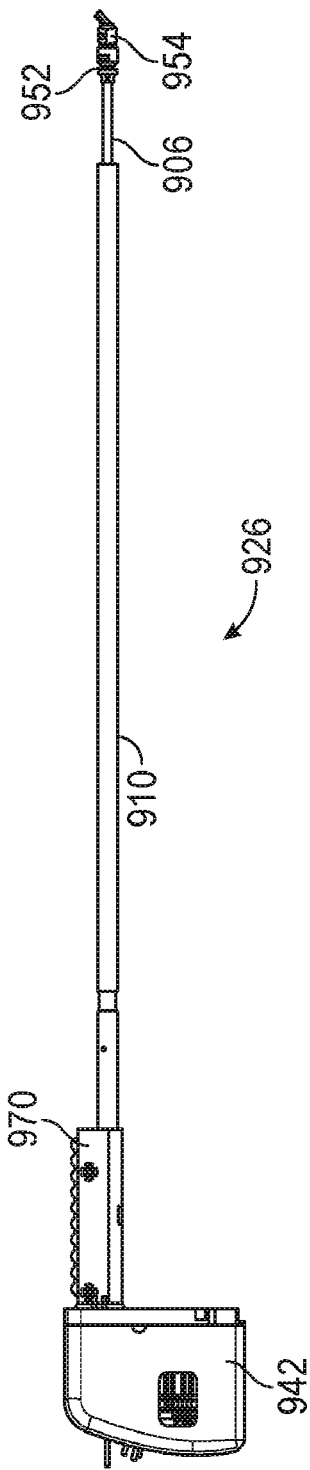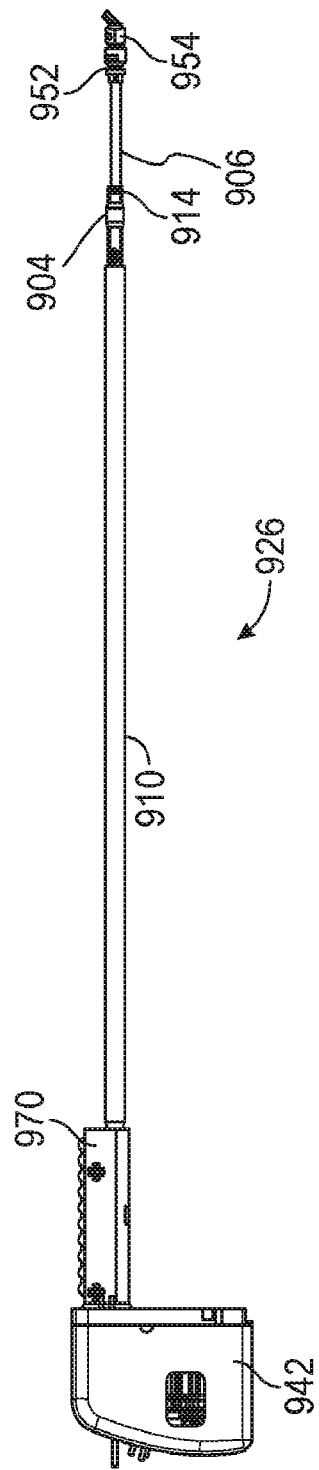

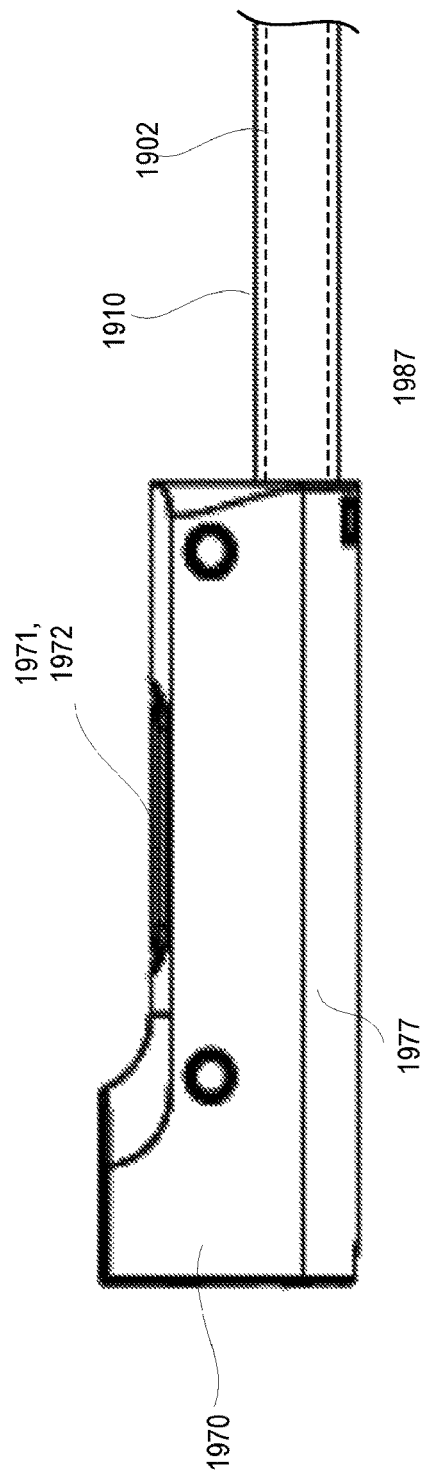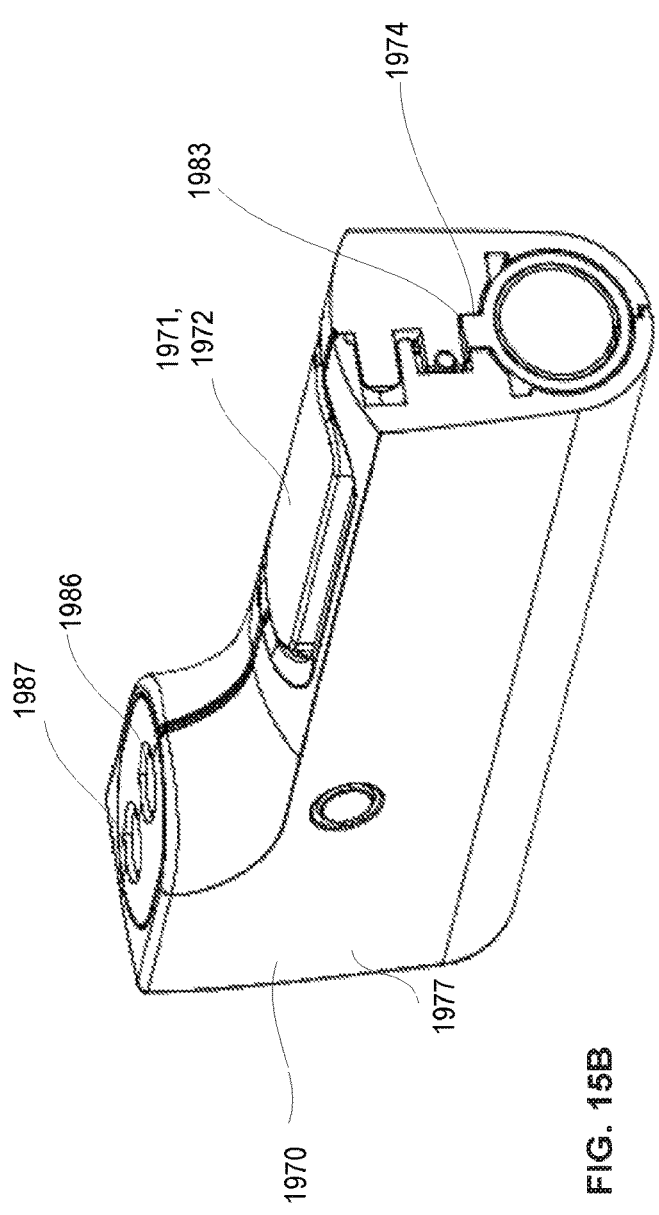

SURGICAL TOOL WITH NESTED SHAFT TUBES

CROSS-REFERENCE TO RELATED APPLICATIONS

This patent application is a U.S. national stage filing under 35 U.S.C. § 371 of International Application No. PCT/US2020/055794, entitled "SURGICAL TOOL WITH NESTED SHAFT TUBES," filed Oct. 15, 2020, which claims priority to and the filing date benefit of U.S. Provisional Patent Application No. 62/916,712, entitled "Surgical Tool with Nested Shafts" and U.S. Provisional Patent Application No. 62/916,716, entitled "Surgical Tool with Nested Shafts" both filed Oct. 17, 2019, the disclosure of each of which is incorporated herein by reference in its entirety.

BACKGROUND

The embodiments described herein relate to medical devices, and still more specifically to instruments used for minimally invasive surgery. More particularly, the embodiments described herein relate to medical devices that include nested shafts that can move relative to each other and to a mechanical structure of the medical device. Still further, embodiments described herein relate to nested shafts that provide fluid pathways for introducing fluids to clean and flush the medical device.

Minimally invasive medical techniques (e.g., endoscopy, laparoscopy, thoracoscopy, cystoscopy, and the like) are intended to reduce the amount of tissue that is damaged during diagnostic or surgical procedures, thereby reducing patient recovery time, discomfort, and deleterious side effects. Minimally invasive surgery allows a patient to be operated upon through small incisions by using a camera and one or more elongated surgical instruments introduced to an internal surgical site. The surgical site often comprises a body cavity, such as the patient's abdomen. The body cavity may optionally be distended using a clear fluid such as an insufflation gas, typically $CO_2$. One or more cannulas may be passed through small (generally 7 cm or less) incisions or a natural body orifice to provide entry ports for the minimally invasive (e.g., endoscopic, laparoscopic, and the like) surgical instruments, including a camera instrument (e.g., endoscope, laparoscope, and the like). A surgeon is able to perform surgery by manipulating the surgical instruments from outside the body while viewing the instrument end effectors at the internal surgical site with images provided by the camera instrument.

Teleoperated surgical systems that use robotic technology are used to overcome limitations of manual laparoscopic and open surgery. Advances in telepresence systems provide surgeons views inside a patient's body, an increased number of degrees of motion of surgical instruments, and the ability for surgical collaboration over long distances. In teleoperated surgery systems, an instrument operator may actuate an input to a master control device to send control signals to a mechanical control device at a proximal end portion of an elongated instrument shaft to control motion of a connector, such as a cable, or a cable-hypotube combination (which functions as a connector) that extends within a length of the shaft, to control movement of an end effector at a distal end portion of the instrument shaft. Control connectors or cable-hypotube combinations, typically are pre-tensioned to enable a surgical instrument at a surgical site to respond rapidly and accurately to actuation signals. Thus, direct natural force feedback to an instrument operator is eliminated because such instrument user does not manually manipulate the instrument directly.

Force sensors at or near an instrument shaft measure clinical forces imparted to patient tissue during a medical procedure due to contact with an end effector, for example. These force measurements at or near an instrument shaft are used to provide an indication of the forces imparted by the instrument to patient tissue, for example. During a medical procedure, however, external forces may be imparted to the instrument shaft other than forces due to contact between an end effector and patient tissue. For example, as the instrument shaft is advanced/retracted in an axial direction (arbitrarily, the z axis in a Cartesian reference frame) within a cannula, an axial friction force may be imparted to the instrument shaft due to contact with the cannula and the cannula seal. And, this axial friction may be inconsistent due to static/dynamic, stick/slip, and non-linear velocity dependencies. As a result, if an axial force sensor is located at an end of an instrument opposite from the end effector, a considerable amount of axial force "noise" may be sensed in addition to the axial force between instrument and tissue.

Thus, there is a need during a medical procedure to isolate external axial friction force imparted to an instrument shaft, such as a friction force due to contact between the instrument shaft and a cannula seal device, from axial clinical forces imparted to the instrument shaft due to contact with tissue within a body cavity. Safe reuse of a surgical instrument requires sterilization/cleaning. Cleaning fluid typically is used to clean/sterilize a surgical instrument after use and prior to reuse. The cleaning fluid is used to flush contaminants from the instrument. Fluid conduits within an instrument shaft have been used to guide fluid flow between a cleaning fluid source and portions of an instrument to be cleaned. A challenge to instrument cleaning arises due to interior small size dimensions within the shaft. Instrument shaft diameters typically are in a range 5-12 mm. Another challenge is the presence of force sensors near the distal end of an instrument shaft that can impede the flushing of the interior space of the shaft. Thus, a need also exists for improved instrument cleaning mechanisms.

SUMMARY

This summary introduces certain aspects of the embodiments described herein to provide a basic understanding. This summary is not an extensive overview of the inventive subject matter, and it is not intended to identify key or critical elements or to delineate the scope of the inventive subject matter. In some embodiments, a surgical instrument is provided that includes a chassis, an outer tube including an outer tube proximal portion, an outer tube distal portion and an inner surface. The inner tube extends within the outer tube and comprises an inner tube proximal portion and an outer surface. A slip interface bushing is between the outer surface of the inner tube and the inner surface of the outer tube. A center axis is defined through the outer tube proximal portion and the outer tube distal portion. The outer tube proximal portion is coupled to the chassis and the inner tube proximal portion is coupled to the chassis such that the inner tube moves along the center axis with reference to the outer tube.

In some embodiments, the outer tube is slidably coupled to the chassis. In some embodiments, the outer tube is slidably coupled to the chassis via a handle that defines a proximal limit of travel of the outer tube with reference the chassis and a distal limit of travel of the outer tube with reference to the chassis.

In some embodiments, the slip interface bushing is fixedly coupled to the outer surface of the inner tube and slidably contacts the inner surface of the outer tube. In some embodiments, the slip interface bushing includes an inner perimeter fixedly coupled to the outer surface of the inner tube and includes an outer perimeter that defines a slip interface in slidable contact with the inner surface of the outer tube. In some embodiments, the slip interface bushing has a bushing inner surface and a bushing outer surface, where the bushing inner surface is fixedly coupled to the outer surface of the inner tube and the bushing outer surface is chamfered and forms a slip interface with the inner surface of the outer tube.

In some embodiments, the inner tube comprises an inner tube distal portion, the slip interface bushing is a first slip interface bushing and is between the outer surface of the inner tube and the inner surface of the outer tube at the inner tube distal portion. The surgical instrument further comprises a second slip interface bushing between the outer surface of the inner tube and the inner surface of the outer tube at the inner tube proximal portion.

In some embodiments, the interface bushing maintains the outer surface of inner tube spaced apart from the inner surface of outer tube. In some embodiments, the inner tube proximal portion is coupled to the chassis such that the inner tube is rotatable with reference to the outer tube. In some embodiments, the surgical instrument further includes a coupler coupling the inner tube proximal portion to the chassis. The inner tube has an inner tube center axis and the coupler includes a contact portion coupled to move in relation to the chassis in response to movement of the inner tube along the inner tube center axis.

In some embodiments, the surgical instrument further includes a force sensor and the coupler is operably coupled to impart a force to the force sensor in response to movement of the contact portion in relation to the chassis. In some embodiments, the coupler includes a four-bar linkage operatively coupling the inner tube to the chassis.

In some embodiments, the surgical instrument further includes a force sensor coupled to the chassis and the coupler includes a four-bar linkage coupling the inner tube to the chassis, the four-bar linkage being operably coupled to impart a force to the force sensor in response to movement of the inner tube along the inner tube center axis.

In some embodiments, a surgical instrument comprises a chassis, an outer tube comprising an outer tube proximal portion and an outer tube distal portion, and an inner tube extending within the outer tube and comprising an inner tube proximal portion. A center axis is defined through the outer tube proximal portion and the outer tube distal portion. The outer tube proximal portion is coupled to the chassis such that the outer tube is moveable along the center axis with reference to the chassis between a proximally retracted position and a distally extended position. The inner tube proximal portion is coupled to the chassis such that the inner tube moves along the center axis with reference to the outer tube.

In some embodiments, the surgical instrument further comprises a cantilever portion. The inner tube further comprises an inner tube distal portion, and the cantilever portion of the surgical instrument distally extends from the inner tube distal portion. The outer tube surrounds at least a first length of the cantilever portion in the distally extended position of the outer tube and the outer tube surrounds less than the first length of the cantilever portion in the proximally retracted position. In some embodiments, one or more force sensors is coupled to the cantilever portion.

In some embodiments, the outer tube is configured to be locked in the proximally retracted position. In some embodiments, the outer tube is configured to be locked in the distally extended position. In some embodiments, the inner tube is configured to move along the center axis without constraint.

In some embodiments, the surgical instrument further comprises a handle coupled to the chassis. The outer tube extends along the center axis within the handle and the handle is configured to lock the outer tube in at least one of the proximally retracted position or the distally extended position. In some embodiments, the outer tube includes a first locking feature and the handle includes a second locking feature. The first and second locking features are configured to be interlockable when the outer tube is in the distally extended position.

In some embodiments, a surgical instrument comprises a chassis, an outer tube comprises an outer tube proximal portion, an outer tube distal portion, and an inner surface, and an inner tube comprises an inner tube proximal portion and an outer surface. The inner tube extends within the outer tube such that a first passage is defined between the inner surface of the outer tube and the outer surface of the inner tube. The outer tube comprises a first fluid port and configured to convey a volume of fluid through the first fluid port and either into or out of the first passage, and the inner tube comprises a second passage and a second fluid port. The second fluid port is configured to convey the volume of fluid between the first passage and the second passage.

In some embodiments, the second fluid port is at the inner tube distal portion, the inner tube comprises a third fluid port at the inner tube proximal portion, and the third fluid port is located to receive the volume of fluid from the second passage.

In some embodiments, the first fluid port is configured to convey the volume of fluid out of the first passage, the second fluid port is at the inner tube distal portion, and the inner tube comprises a third fluid port at the inner tube proximal portion. The third fluid port is located to receive the volume of fluid through the third fluid port.

In some embodiments, the first fluid port is at the outer tube proximal portion, the outer tube comprises a fourth fluid port at the outer tube distal portion, and the fourth fluid port located to convey the volume of fluid either into or out of the first passage through the fourth fluid port.

In some embodiments, a center axis is defined through the outer tube proximal portion and the outer tube distal portion, and the outer tube proximal portion is coupled to the chassis such that the outer tube is moveable along the center axis with reference to the chassis between a proximally retracted position and a distally extended position. The fourth fluid port is configured to convey the volume of fluid either into or out of the first passage through the fourth fluid port when the outer tube is in the retracted position.

In some embodiments, the surgical instrument comprises a handle coupled to the chassis, and the outer tube is moveable along the center axis within the handle with reference to the chassis between the proximally retracted position and the distally extended position. The handle is configured to lock the outer tube in at least one of the proximally retracted position or the distally extended position.

In some embodiments, the surgical instrument further comprises a handle coupled to the chassis and the handle comprises a handle port. The outer tube is moveable along the center axis within the handle such that when the outer tube is in the distally extended position, the handle port is aligned with the first fluid port. In some embodiments, the outer tube is configured to convey the volume of fluid through the first fluid port and into the first passage when the handle port is aligned with the first fluid port.

In some embodiments, the surgical instrument further comprises a slip interface bushing between the outer surface of the inner tube and the inner surface of the outer tube. The slip interface bushing is fixedly coupled to the inner tube and is moveably coupled to the outer tube. The fourth fluid port is configured to convey the volume of fluid either into or out of the first passage through the fourth fluid port when the outer tube is in the proximally retracted position, and the fourth fluid port is proximally spaced from the slip interface bushing.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIGS. 8A-8B are illustrative side views of a surgical instrument that includes a handle which functions to alternately position an outer tube in an extended position (FIG. 8A) and a retracted position (FIG. 8B).

FIG. 15A is a side view of a portion of a surgical instrument according to an embodiment.

FIG. 15B is a perspective cross-sectional view of a portion of the surgical instrument of FIG. 15A.

DESCRIPTION OF EMBODIMENTS

Figure 1:
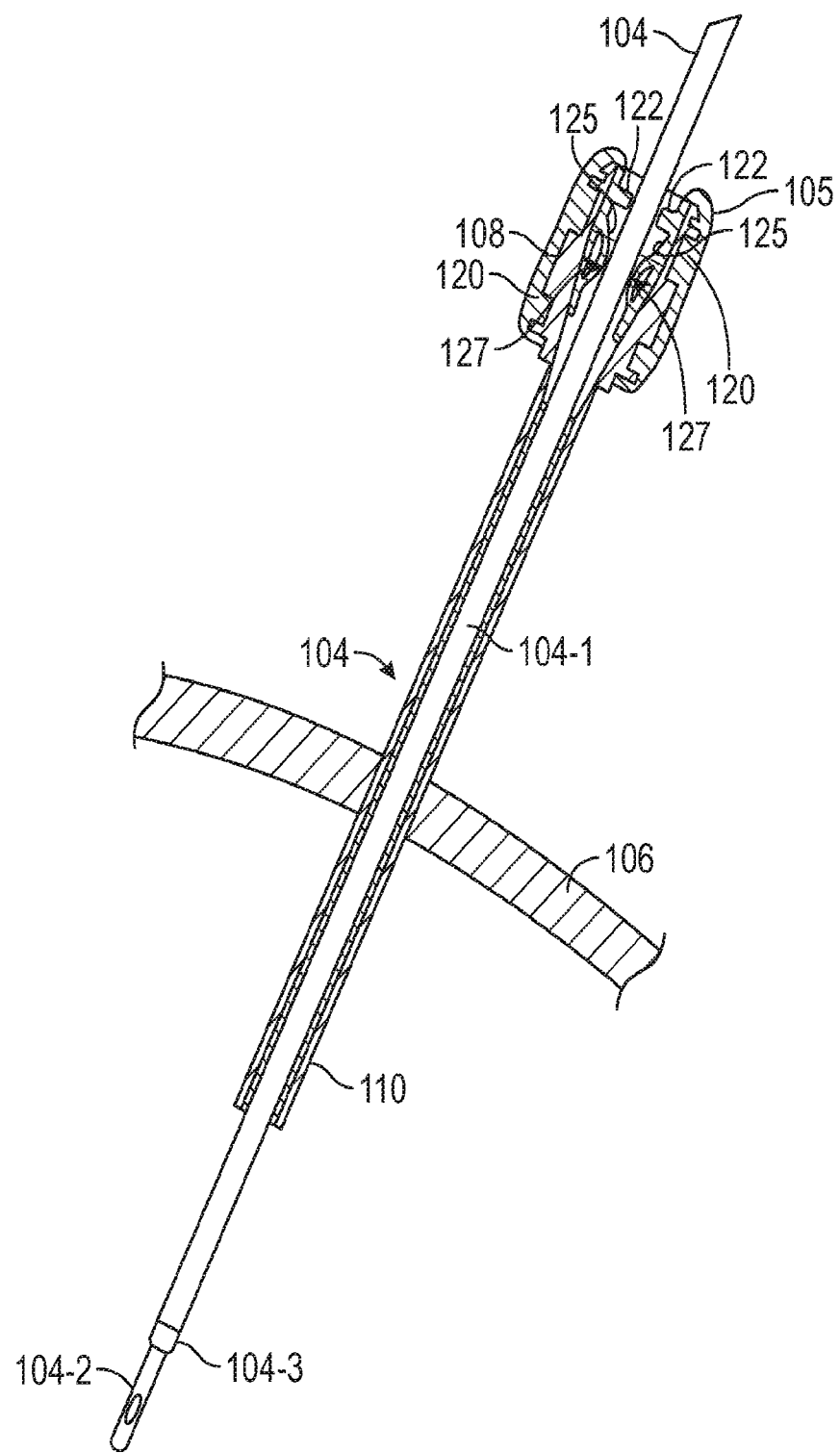
FIG. 1 is an illustrative perspective cross-sectional view showing an example surgical instrument extending within a cannula at a patient body wall to provide access to a patient's body cavity.

FIG. 1 is an illustrative perspective cross-sectional view showing an example surgical instrument 104 extending within a cannula 105 disposed at a patient body wall 106 to provide access to a patient's body cavity. The surgical instrument 104 includes an instrument shaft 104-1, an end effector 104-2 and a joint (such as a wrist assembly) 104-3. The cannula 105 includes a proximal end portion 108 and a distal end portion 110. The cannula 105 acts as a conduit for passage of the instrument shaft 104-1 and the end effector 104-2 through a patient's body wall 106. During a medical procedure, the cannula distal end 110 portion extends within the patient body cavity, while the cannula proximal end portion 108 is disposed outside the patient's body wall 106. During a minimally invasive medical procedure, the body cavity typically is insufflated with an inert gas to provide additional work room for the surgical instrument, for example. Often, an insufflation seal device is used to prevent escape of insufflation gas. PCT Application PCT/US2019/031393 (filed May 18, 2019) (entitled "Instrument Seal") the disclosure of which is incorporated herein by reference, discloses an example insufflation seal device for use with a cannula that provides a small opening to allow passage of an instrument shaft while minimizing gas leakage. One insufflation seal device 120 includes a housing 122, a proximal annular seal 125 and a distal cross-slit seal 127. The seal housing 122 snaps into the cannula proximal end portion 108 and surrounds the proximal end portion 108 to prevent escape of the inert gas between the proximal end portion 108 and the patient body wall 106. The annular seal 125 and the cross-slit seal 127 portions of the seal device 120 extend within the cannula proximal end portion 108 to prevent escape of the inert gas between the surgical instrument shaft 104-1 and the proximal end portion 108. During a medical procedure, the outer surface of elongated shaft 104-1 mechanically contacts the insufflation seal. Often during a medical procedure, axial friction force is imparted to the instrument shaft 104-1 as the shaft moves axially by small amounts while in contact with the insufflation seal 120. Frictional force imparted due to contact with the seal device 120 is imparted to force sensors (not shown) disposed to measure clinical forces imparted to patient tissue within the body cavity. The presence of axial friction forces due to contact between the seal device 120 and the shaft 104-1 can be difficult to isolate from axial clinical forces imparted to the instrument 104 due to contact between the end effector 104-2 and patient tissue, for example. Thus, there is a need during a medical procedure to isolate external axial friction forces imparted to an instrument shaft 104-1, such as a friction force due to contact between an instrument shaft 104-1 and a cannula seal device 105, from axial clinical forces imparted to the instrument shaft 104-1 due to contact with tissue within the body cavity.

Teleoperated Surgical System

Figure 2:
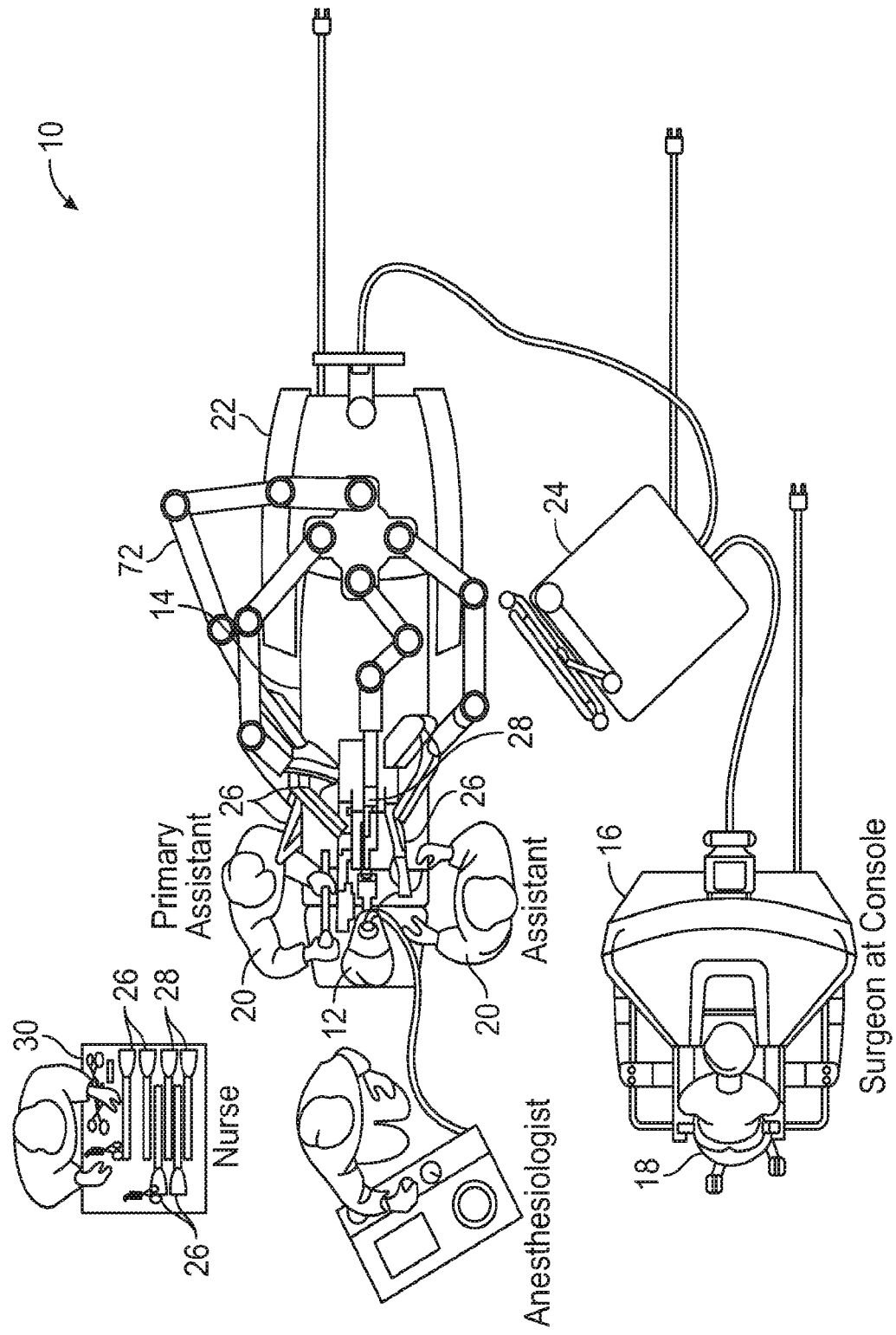
FIG. 2 is an illustrative plan view of a minimally invasive teleoperated surgical system for performing a minimally invasive diagnostic or therapeutic surgical procedure on a patient who is lying on an operating table.

FIG. 2 is an illustrative plan view of an example minimally invasive teleoperated surgical system 10 for performing a minimally invasive diagnostic or surgical procedure on a patient 12 who is lying on an operating table 14. The system includes a user control system 16 for use by a surgeon 18 during the procedure. One or more assistants 20 also may participate in the procedure. The minimally invasive teleoperated surgical system 10 further includes a patient-side cart 22 that includes a manipulator system, and an auxiliary system 24. The patient-side cart 22 can manipulate at least one surgical instrument 26 through a minimally invasive incision in the body of the patient 12 while the surgeon 18 views a video image of the surgical site through the user control system 16. An image of the surgical site can be obtained by an endoscope 28, such as a stereoscopic endoscope, which is inserted through a cannula and positioned using a manipulator support structure 72 associated with the patient-side cart 22 to orient the endoscope 28 to capture images of the surgical site. One or more computer processors located on the electronics cart 24 are used to process the images of the surgical site for subsequent display to the surgeon 18 through the user control system 16. Moreover, one or more computer processors at the electronics cart 24 are configured to process electronic or optical signals indicative of forces imparted at the surgical instrument. The computer processors produce haptic feedback output on one or more input devices at the user control system 16, for example. In some embodiments, stereoscopic images are captured, which allow the perception of depth during a surgical procedure. The number of surgical instruments 26 used at one time will generally depend on the diagnostic or surgical procedure and the space constraints within the operative site among other factors. If it is necessary to change one or more of the surgical instruments 26 being used during a procedure, an assistant 20 may remove the surgical instrument 26 from the manipulator support structure 72 associated with patient-side cart 22 and replace it with another surgical instrument 26 from a tray 30 in the operating room.

Figure 3:
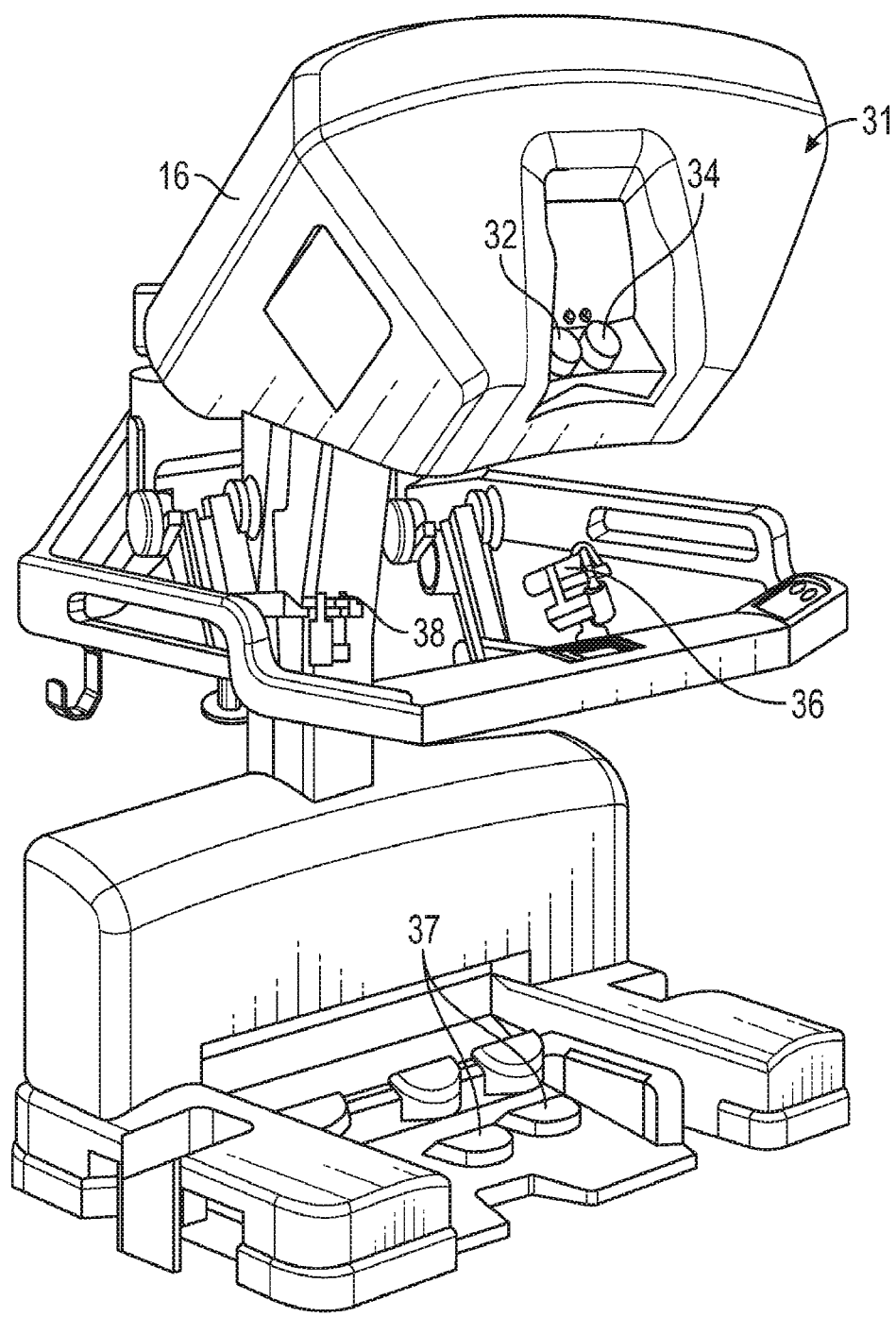
FIG. 3 is a perspective view of a user control system.

FIG. 3 is a perspective view of the user control system 16. The user control system 16 includes a viewer display system 31 that includes a left eye display 32 and a right eye display 34 for presenting the surgeon 18 with a coordinated stereoscopic view of the surgical site that enables depth perception. The user control system 16 further includes one or more hand-operated user input devices 36, 38 to receive the larger-scale hand control movements. One or more slave surgical instruments 26 installed for use at on one or more corresponding manipulator support structures 72 of the patient-side cart 22 move in smaller-scale distances that match a surgeon 18's larger-scale manipulation of the one or more master control inputs 36, 38. The master control inputs 36, 38 provide at least the same mechanical degrees of freedom as their associated surgical instruments 26 to provide the surgeon 18 with telepresence, or the perception that the master control inputs 36 are integral with the slave surgical instruments 26 so that the surgeon has a keen sense of directly controlling the instruments 26. To this end, position, force, and/or tactile feedback sensors (not shown) are employed to determine tool position, and to measure force, and to measure tactile sensation at the instruments 26. The determined instrument position and force is used to produce haptic feedback at a surgeon's hands through the control inputs 36, 38. Electrical or optical signals modulated based upon forces detected at force sensors (not shown) at the instrument 26 are processed by the processors at the electronics cart 24 to produce the haptic feedback at the control inputs 36, 38 that are indicative of magnitude and direction of the detected forces.

Figure 4:
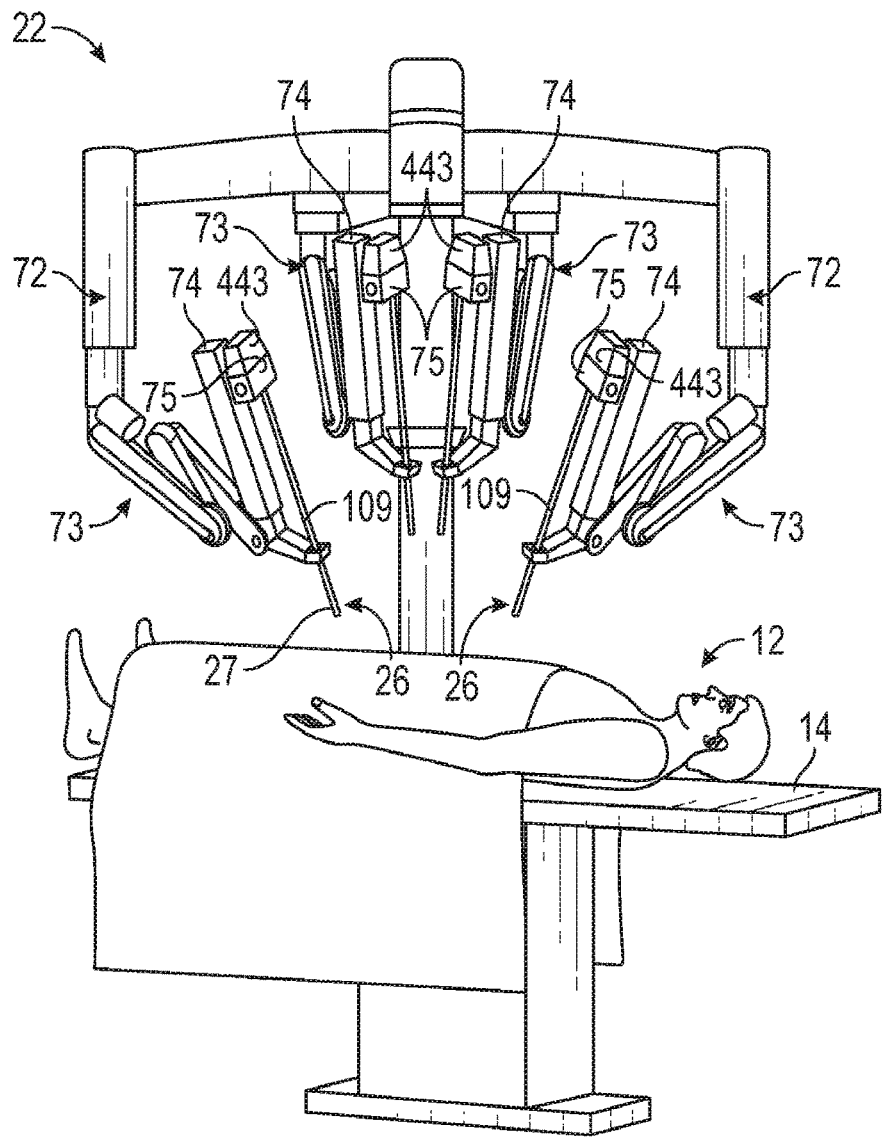
FIG. 4 is a perspective view of a patient-side cart of a minimally invasive teleoperated surgical system.

FIG. 4 is a perspective view of a patient-side cart 22 of the example minimally invasive teleoperated surgical system 10, in accordance with some embodiments. The patient-side cart 22 includes four manipulator support structures 72. Each manipulator support structure 72 includes articulated support structures 73 that are pivotally mounted end-to-end and a pivotally mounted support structure forearm 74. A respective surgical instrument carriage 75, which includes motors to control instrument motion, is mounted at each support structure forearm 74. Additionally, the manipulator support structure 72 can optionally include one or more setup joints (e.g., unpowered and/or lockable) at the junctions of the articulated support structures 73 and at the junction with the support structure forearm 74 that are used to position the attached surgical instrument carriage 75 in relation to a patient 12 for surgery. Each surgical instrument 26 is detachably connected to a carriage 75. While the patient-side cart 22 is shown as including four manipulator support structure 72, more or fewer manipulator support structures 72 may be used. In general, at least one of the surgical instruments will include a vision system that typically includes an endoscopic camera instrument for capturing video images and one or more video displays for displaying the captured video images that are coupled to one of the carriages 75.

In one aspect, for example, a surgical instrument 26 is removably coupled to a carriage 75, a cannula is coupled to a manipulator support structure 72, and an instrument shaft portion, of the surgical instrument 26, such an outer tube 410 shown in FIG. 4, is inserted through the cannula 27. In one aspect, the carriage 75 houses multiple teleoperated actuators such as motors (not shown) that impart motion to a tension member, such as a cable drive member. The teleoperated actuators include drive shafts and capstans (not shown), that in turn, drive cable motions that the surgical instrument 26 translates into a variety of movements of an end effector portion of the surgical instrument 26. In some embodiments, the teleoperated actuators in the carriage 75 impart motion to individual components of the surgical instrument 26 such as end effector wrist movement or jaw movement, for example.

Z-Axis Friction Force Isolation

Figure 5:
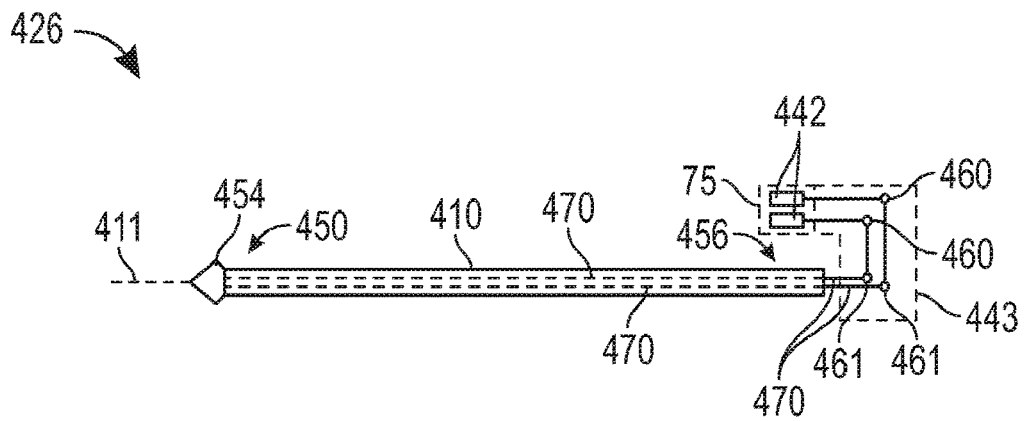
FIG. 5 is a diagrammatic view of a surgical instrument coupled to a carriage.

FIG. 5 is a diagrammatic view of a surgical instrument 426 coupled to a carriage 75. The surgical instrument 426 includes an elongated outer tube 410 having a distal end portion 450 that includes an end effector 454 for insertion into a patient's body cavity and a proximal chassis 443 (see also FIG. 4). An inner wall of the outer tube 410 defines a hollow bore. As explained more fully below, an inner tube (not visible) is nested coaxially within the outer tube 410. The outer tube 410 includes a longitudinal center axis 411 (a "shaft center axis") that is defined between the proximal and distal ends of the shaft. As used herein the term proximal indicates a location at a surgical instrument closer to a manipulator support structure and the term distal indicates a location at a surgical instrument more distant from the manipulator support structure. The outer tube 410 and inner tube (not visible) are mounted together on the proximal chassis 443 (shown transparent in FIG. 5, and indicated with dashed lines) in a coaxial nested relation in parallel alignment with the center axis 411. Also coupled within the chassis 443 are multiple cable drive members 460, which may include one or more capstans and drive shafts, for example, and pulleys 461 that are configured to couple drive torques or forces imparted by one or more actuators 442 within a carriage 75, to cables 470 extending within the inner tube (not visible). The connectors 470 extend within the inner tube between the drive members 460 and an end effector 454. In some embodiments, the connectors 470 can be a cable, a band or the like. The connectors 470 are operatively coupled so that movement of the connectors 470 may impart motion to the end effector 454, such as to open or close jaws, and such as to effect translation or orientation of the end effector 454 via wrist motion, for example. The end effector 454 can include a functional mechanical degree of freedom, such as jaws that open or close, or a knife that translates along a path or a wrist 452 (shown in FIG. 6) that moves in x and y directions. U.S. Pat. No. 6,394,998 B1 (filed Sep. 17, 1999), which is incorporated herein by reference, shows examples of connector-controlled end effectors with multiple mechanical degrees of freedom (DOFs). The distal portion 450 of the instrument 426 can provide any of a variety of different kinds of end effectors 454, such as forceps, a needle driver, a cautery device, a cutting instrument, an imaging device (e.g., an endoscope or ultrasound probe), or the like. Thus, actuators 442 (such as motors) located at the carriage 75 near the proximal end portion 456 of the shaft 410 control movement of the end effector 454 at the distal end portion 450 of the shaft 410 by causing drive members 460 within the chassis 443 to exert control forces upon the connectors 470 that are extending within the shaft 410 parallel to the shaft center axis 411 between the drive members 460 and the end effector 454.

Figure 6:
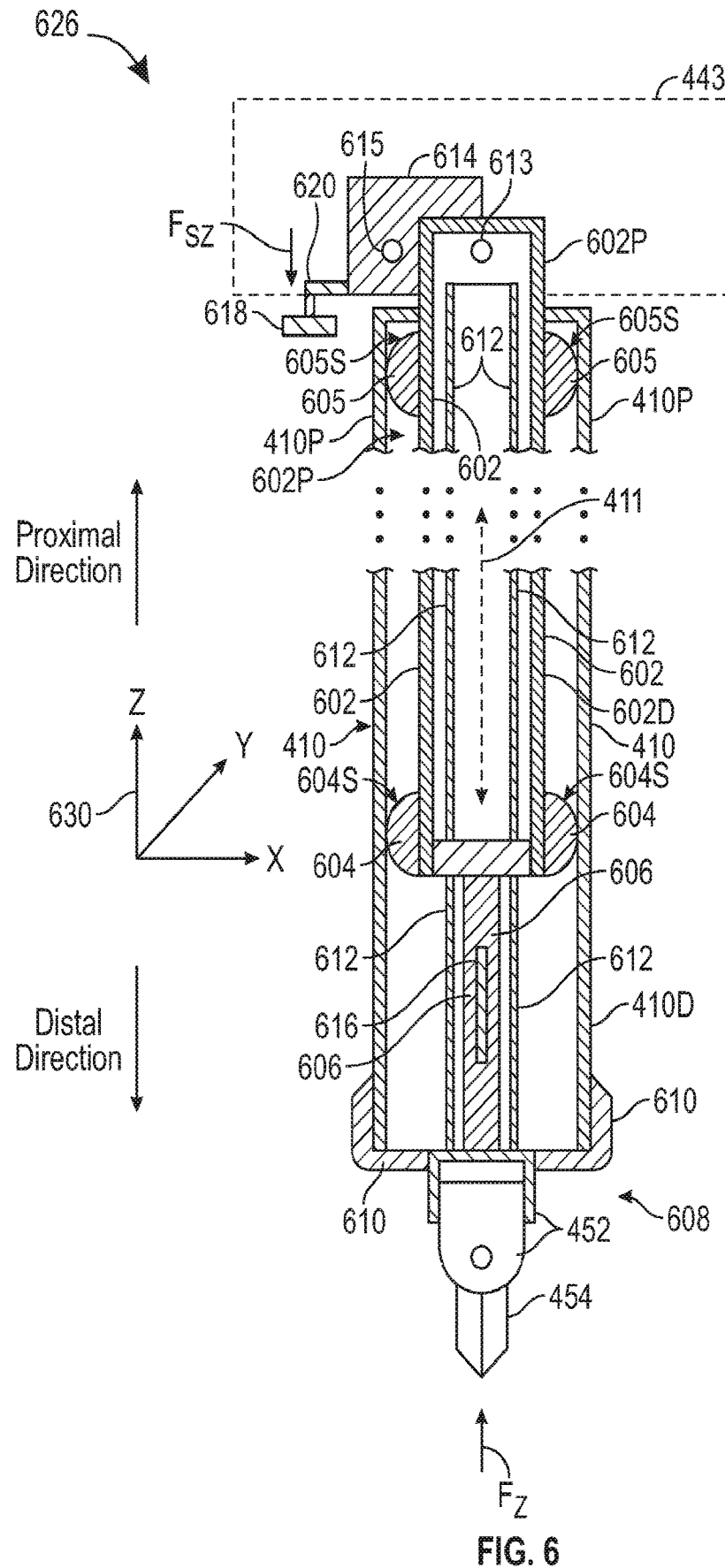
FIG. 6 is an illustrative cross-sectional partially cut-away side view of an example surgical instrument that includes an inner tube coaxially nested within an outer tube.

FIG. 6 is an illustrative diagrammatic cross-sectional side view of an example surgical instrument 626 that includes a proximal chassis 443, a hollow outer tube 410, a hollow inner tube 602 coaxially nested within the outer tube 410, a distal slip interface bushing 604, a proximal slip interface bushing 605, a cantilever beam portion 606 extending from an inner tube distal portion 602D, and an end effector 454 extending from a distal portion of the cantilever beam portion 606. Certain components of the surgical instrument 626 are similar to those described above with reference to the surgical instrument 426, such as the outer tube 410. Thus, certain features described as being included in the surgical instrument 426 can be included in the surgical instrument 626, and vice-versa. Example end effectors include clamps, graspers, scissors, staplers, needle holders, cauterization terminals, endoscopes, and ultrasound probes, to name a few. A wrist assembly 608 provides multiple degrees of freedom for positioning end effector 454. As shown in FIG. 6, an example wrist assembly 608 includes a clevis assembly 452 that extends from the distal portion of the cantilever beam portion 606 to allow rotational motion of the end effector 454 about the x-axis (arbitrarily designated pitch) and the y-axis (arbitrarily designated yaw) of the Cartesian reference frame 630 as shown. Other single- or multiple-DOF wrist assembly designs may be used. A coupling (e.g., a flexible coupling) 610 seals a gap between the distal end 410D of the outer tube 410 and the clevis assembly 452 while allowing relative translational motion between the outer tube 410 and clevis assembly 452 along the z-axis (arbitrarily designated insertion) of reference frame 630 and with a low stiffness so as to not affect the X and Y sensor readings. In some embodiments, the coupling 610 may not seal the gap tightly to permit the beam to deflect without interference in X and Y directions. In such cases, the bushing 604 provides a close fit between the inner tube 602 and the outer tube 604 to prevent or reduce leakage. Actuation connectors and/or hypotube rods 612 operably coupled to actuators (not shown), which are mounted at the chassis 443, extend within the inner tube 602 and are operably coupled to the wrist assembly 608 and/or the end effector 454. The connectors or hypotube 612 rods fit within the inner tube 602 and control the end effector 454 through the wrist assembly 608. The connectors or hypotubes 612 are manufactured from a variety of metal (e.g., tungsten or stainless steel) or polymer (e.g., high molecular weight polyethylene) materials.

The outer tube 410 includes an outer tube proximal portion 410P and the outer tube distal portion 410D, with a center axis 411 extending between the proximal portion 410P and distal portion 410D. The inner tube 602 includes the inner tube proximal portion 602P and the inner tube distal portion 602D extending along the center axis 411. The inner tube 602 extends coaxially within the outer tube 410. The distal slip interface bushing 604 is secured around the inner tube distal portion 602D and contacts an inner surface of the outer tube distal portion 410D. In some embodiments, the slip interface bushing 604 includes an inner perimeter fixedly coupled to an outer surface of the inner tube 602 and includes an outer perimeter that defines a slip interface in slidable contact with the inner surface of the outer tube 610. In some embodiments, the distal slip interface bushing 604 has a bushing inner surface that is fixedly coupled to the outer surface of the inner tube 602 and a bushing outer surface that is chamfered and forms a slip interface with the inner surface of the outer tube 610. Similarly, the proximal slip interface bushing 605 is between the outer surface of the inner tube 602 and the inner surface of the outer tube 610 at the inner tube proximal portion 602P. The slip interface bushings 604, 605 each can maintain the outer surface of inner tube 602 spaced apart from the inner surface of outer tube 610.

Force sensors 616 (e.g., electrical or optical strain sensors) are placed on cantilever beam portion 606 so that transverse forces on end effector 454 in the directions of the x- and y-axes of reference frame 630 are sensed. Signals indicating the sensed forces are produced at force sensors 616 and are communicated to the teleoperated surgical system on which instrument 626 is mounted. The telesurgical system then processes the received signals and outputs corresponding haptic sensations to the hand operating the input device controlling x and y directional movement of end effector 454.

In one aspect, outer tube 410 is configured to slide in proximal and distal directions (i.e., in the direction of the z-axis of reference frame 630, along the center axis 411) relative to the inner tube 602 and instrument chassis 443. In other aspects, the outer tube 410 optionally may be fixedly secured at a proximal or distal position relative to inner tube 602, chassis 443 or both. During normal clinical operation of instrument 626, the outer tube proximal portion 410P is positioned such that at a distal position relative to the chassis 443, and the outer tube distal portion 410D extends over the distal slip interface bushing 604 and about at least a portion of the cantilever beam portion 606. During a post-operative cleaning operation performed on instrument 26, the outer tube 410 is moved such that the proximal portion 410P is moved to a proximal position relative to chassis 443.

In another aspect, the inner tube 602 is configured to move in proximal and distal directions (i.e., in the direction of the z-axis of reference frame 630, along the center axis 411) relative to instrument chassis 443, and also relative to outer tube 410. In some embodiments, the outer tube 410 is fixedly secured to chassis 443 when the inner tube 602 moves relative to the outer tube 410. The inner tube proximal portion 602P is coupled to a contact portion of a coupler 614. An example contact portion includes a first pivot axis 613. The coupler 614 is coupled at a second pivot axis 615 to the chassis 443. The first and second pivot axes 613, 615 cooperate to permit motion of the coupler 614 in response to movement of the inner tube 602 along the center axis 411. More particularly, the first pivot axis 613 moves in a direction parallel to the center axis 411 in response to movement of the inner tube 602 parallel to the center axis 411. The coupler 614 is coupled to move in unison with the inner tube 602. During sliding motion of the inner tube 602 within the outer tube 410, the distal slip interface bushing 604 provides a low friction slip interface surface 604S between a distal portion of an inner surface of the outer tube 410 and a distal portion of an outer surface of the inner tube 602. More particularly, an outer slip interface surface 604S of the distal slip interface bushing 604 at an outer peripheral surface of the distal slip interface bushing 604 slidably contacts an inner surface of the outer tube 410. Similarly, the proximal slip interface bushing 605 provides a low friction slip interface 605S between a proximal portion of the inner surface of the outer tube 410 and a proximal portion of the outer surface of the inner tube 602. As used herein, the term slip interface refers to an interface with a lower coefficient of friction than a coefficient of friction between a bare outer surface of the inner tube 602 and a bare inner surface of the outer tube 410. An example slip interface surface has a coefficient of friction <0.15 (e.g., PTFE-Steel≈0.05).

As mentioned above, transverse (i.e., in the direction of the x- and y-axes of reference frame 630, normal to the center axis 411) force sensors 616 (only one is shown) coupled to the cantilever beam portion 606 measure transverse forces imparted to the end effector 454 in a direction transverse to the center axis 411. A transverse force acting upon the end effector 454 causes a slight flex of the beam 606, which results in a tensile strain imparted to one side of the beam 606 and a compressive strain imparted to the opposite side of the beam 606. The transverse strain sensors 616 are coupled to the beam 606 to measure such tensile and compression forces.

An axial (i.e., in the direction of the z-axis of reference frame 630, along the center axis 411) force sensor 618 is operably coupled to the coupler 614 to measure an axial force imparted to the end effector 454 parallel to the center axis 411. An axial force sensor in one example surgical instrument comprises a deflectable planar diaphragm sensor that deflects in response to a force. Alternatively, a deflectable ferrite core within an inductive coil may be used, or a fiber Bragg grating formed within an optical fiber can be used, for example. Other axial force sensor designs may be used to sense a resilient axial displacement of inner tube 602. An axial force $F_Z$ imparted to the end effector 454 causes axial displacement of the inner tube 602 within the outer tube 410 in a direction along the center axis 411, causing a corresponding motion of the displaceable coupler 614. The axial force $F_Z$ may be in the proximal direction (e.g., a reactive force resulting from pushing against tissue with the end effector) or it may be in the distal direction (e.g., a reactive force resulting from pulling tissue grasped with the end effector). The coupler 614 includes a flexible beam structure 620 configured to couple to the axial force sensor 618 to measure a force $F_{SZ}$ corresponding to the axial force imparted to the inner tube 602. Details of an example coupler 614 that includes a four-bar linkage coupling are provided in U.S. Provisional Application No. 62/767,885 (filed Nov. 15, 2018) (entitled "Decoupling Tool Shaft From Cable Load"), and U.S. Provisional Application No. (filed Sep. 14, 2020) (entitled "Devices and Methods for Compact, Redundant Inductive Force Sensor"), each of which is expressly incorporated herein in its entirety by this reference.

Figure 7B:
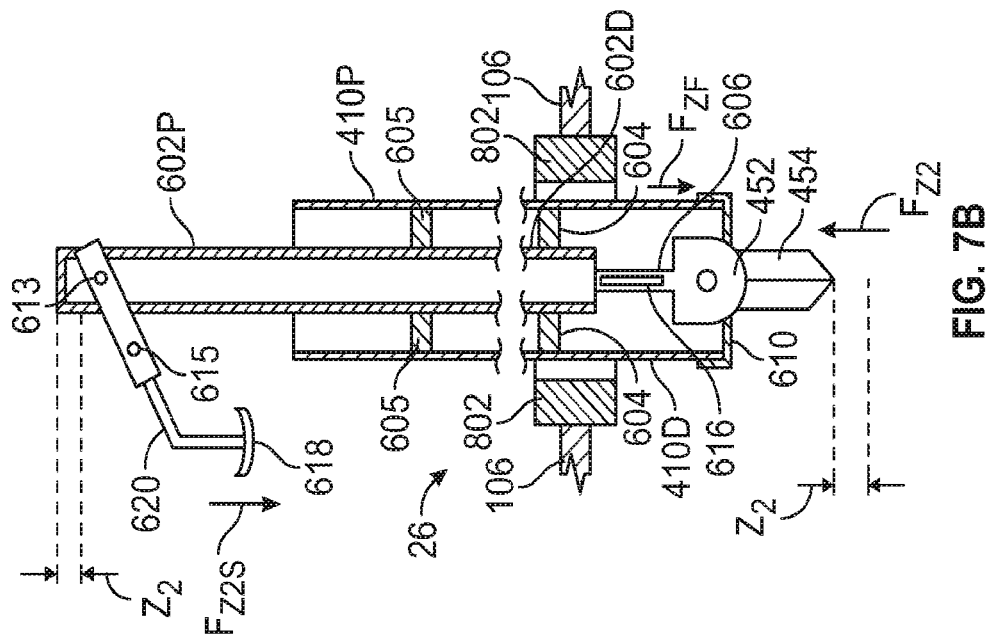
FIG. 7B is an illustrative diagrammatic cross-sectional partially cut-away view of the surgical instrument of FIG. 6 showing the inner tube in an example second axial position relative to the outer tube.
Figure 7A:
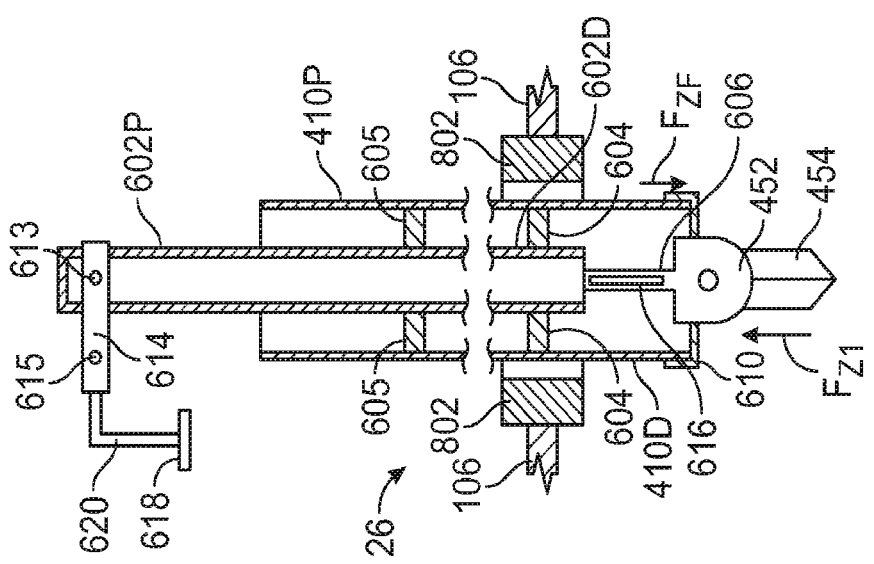
FIG. 7A is an illustrative diagrammatic cross-sectional partially cut-away view of the surgical instrument of FIG. 6 showing an inner tube in an example first axial position relative to an outer tube.

FIG. 7A is an illustrative diagrammatic cross-sectional view of the surgical tool 626 of FIG. 6 showing the inner tube 602 in an example first axial position relative to the outer tube 410. FIG. 7B is an illustrative diagrammatic cross-sectional view of the surgical tool 626 of FIG. 6 showing the inner tube 602 in an example second axial position relative to the outer tube 410. In the illustrative example of FIG. 7A, the first axial position represents a neutral or rest position in which a first axial force $F_{Z1}$ having a magnitude zero is imparted to the end effector 454, which causes corresponding zero axial displacement of the inner tube 602 within the outer tube 410, a corresponding zero displacement of the coupler 614, and a corresponding zero force exerted upon the axial sensor 618. The sensor 618 is shown to be undeflected, at rest, in FIG. 7A.

In the illustrative example of FIG. 7B, the second axial position represents an axially displaced inner tube position in which a second axial force $F_{Z2}$ having greater than zero magnitude is imparted to the end effector 454, which causes a corresponding $Z_2$ axial displacement of the inner tube 602 within the outer tube 410, a corresponding $Z_2$ displacement of the coupler 614 (at the first pivot axis 613), and a corresponding non-zero force $F_{Z2S}$ exerted upon the diaphragm sensor 618, which is shown to be deflected in FIG. 7B.

The surgical instrument outer tube 410 is shown in FIGS. 7A-7B inserted through a cannula 802 that extends through an incision in a patient tissue wall 106. To simplify the explanation, an insufflation seal in the cannula 802 is not shown, although an insufflation seal often is between an outer surface of the instrument shaft (in this situation, the outer surface of the outer tube 410) and an interior surface of the cannula 802 as described above. During a typical medical procedure, the outer tube 410 can be in continuous or intermittent contact with the cannula 802 (or an insufflation seal associated with the cannula), which causes axial-direction friction reaction force $F_{ZF}$ to be imparted to the outer surface of the outer tube 410 due to rubbing contact between the outer tube 410 and the cannula 802 (or the insufflation seal). The low friction outer slip interface surface 604S of the distal slip interface bushing 604 isolates the inner tube 602 from the axial-direction outer tube friction forces $F_{ZF}$. Therefore, due to the low friction sliding between the inner tube 602 and outer tube 410, if the shaft (e.g., outer and inner tubes 410 and 602) of instrument 626 is inserted to a position in which end effector 454 contacts tissue, reaction force produced by this tissue contact is transmitted via inner tube 602 to the proximal end 602P of the inner tube 602 with no interfering frictional component experienced by the outer tube 410. Likewise, if the shaft (e.g., outer and inner tubes 410 and 602) of instrument 626 is withdrawn while end effector 454 is retracting or grasping tissue, reaction force produced by this tissue contact is similarly transmitted via inner tube 602 to the proximal end 602P of the inner tube with no interfering frictional component experienced by the outer tube 410. An example distal slip interface bushing 604 is formed of a low coefficient of friction material such as Teflon, Teflon-filled polymer, or FEP. A circumferential inner surface of the distal slip interface bushing 604 is fixedly secured to the inner tube distal portion 602D. A smooth circumferential outer slip interface surface 604S of the distal slip interface bushing 604 slidably contacts a smooth inner surface of the outer tube 410. In one aspect, the outer surface of the distal slip interface bushing 604 is optionally chamfered so that the outer slip interface surface 604S has a larger diameter near a center portion of the distal slip interface bushing 604 than at distal and proximal end portions of the distal slip interface bushing 604, so as to avoid catching on the outer tube 410, and also, for ease of assembly. Thus, together, the smooth circumferential outer surface of the distal slip interface bushing 604 and the smooth inner surface of the outer tube 410 provide a low friction slip interface that isolates the inner tube 602 from axial direction frictional forces imparted to the outer surface of the outer tube 410. The inner tube 602 and the distal slip interface bushing 604 secured to the distal portion thereof, slide axially within the outer tube 410 in response to axial forces imparted to the end effector 454 due to tissue forces imparted by contact with patient tissue during a medical procedure, for example. The low friction outer slip interface surface 604S of the distal slip interface bushing 604 isolates the inner tube 602 from friction forces imparted to the outer surface of the outer tube 410 due to contact with the cannula 802, for example. Moreover, in one aspect the inner tube 602 is rotatable within the outer tube 610. In some embodiments, the inner tube 602 is rotatable within the outer tube 610, for example, when the outer tube 610 is fixedly secured to the chassis 443 during normal operation. Rotation of the inner tube 602 within the outer tube 604 allows for transmission of roll motion via the inner tube 602 to end effector 454 secured to the inner tube 602.

Anchoring the Cantilever Beam Portion to the Outer Tube

In one aspect, the slip interface bushing 604 is at the distal end of the inner tube and so acts to anchor the cantilever beam portion 606 to the outer tube 410. In this aspect, the full bending moment from a transverse force on the end effector 454 is at the junction between the cantilever beam portion 606 and the distal end of the inner tube 602, and the slip interface bushing 604 at the distal end of the inner tube 602 acts as a transverse anchor to the outer tube 410, which keeps the inner tube 602 from flexing as a result of the transverse force.

In a similar aspect, the distal slip interface bushing 604 is near but not directly at the distal end of the inner tube 602. In this aspect, however, the small distance between the distal slip interface bushing 604 and the junction between the cantilever beam portion 606 and the distal end of the inner tube 602 makes this distal-most portion of the inner tube 602 effectively rigid in relation to transverse forces on the end effector 454 during surgery. And so, the distal slip interface bushing 604 acts to anchor the cantilever beam portion 606 to the outer tube 410. In this aspect, the full bending moment from a transverse force on the cantilever beam portion 606 is also at the junction between the cantilever beam portion 606 and the distal end of the inner tube 602, and the distal slip interface bushing 604 near the distal end of the inner tube 602 acts as a transverse anchor to the outer tube 410, which keeps the inner tube 602 from flexing as a result of the transverse force.

For example, inner tube 602 optionally may be formed of metal, and outer tube 410 optionally is formed of an epoxy material. The metal walls of an example inner tube 602 are thin enough that transverse forces imparted to the cantilever beam portion 606 during a medical procedure could possibly result in flexing of the inner tube 602, which could lead to inaccurate lateral force measurements of clinical forces between an end effector 454 and patient tissue, for example. The outer tube 410 is sturdier and less susceptible to bending due to lateral clinical forces. The distal slip interface bushing 604 between and in contact with the inner tube 602 and outer tube 410 stiffens the inner tube 602 by coupling together the inner tube proximal portion 602P to the outer shaft 410. Thus, the distal slip interface bushing 604 anchors the cantilever beam portion 606, which extends from the inner tube 602 to the sturdier outer tube 410. The cantilever beam portion 606 is then free to deflect within the distal portion 410D of the outer tube 410, but this deflection occurs from the distal end portion 602D of inner tube 602, and the inner tube 602 does not deflect within the outer tube 410. In this way, the strain imparted on the cantilever beam portion 606 accurately corresponds to the transverse force on the end effector 454.

Cleaning and Flushing

FIGS. 8A-8B are illustrative side views of a surgical instrument 926 that includes a handle 970 in which to alternately position an outer tube 910 in an extended distal position (FIG. 8A) and a retracted proximal position (FIG. 8B) in relation to a proximal end chassis 942 of the instrument 926. The handle 970 couples the outer tube 910 to the proximal chassis 942. An inner tube (not shown) is coaxially coupled within the outer tube 910 as described above. In the extended distal position shown in FIG. 8A, the outer tube 910 extends distally over the inner tube (not visible), a distal slip interface bushing 904 (FIG. 8B) and a portion of the cantilever beam portion 906 that includes transverse force sensors 914 (shown in FIG. 8B). The transverse force sensors 914 can, for example, extend along a lengthwise portion of the cantilever beam portion as shown for sensors 616 in FIGS. 6, 7A and 7B. In the retracted proximal position shown in FIG. 8B, the outer tube 910 is retracted within the handle 970 so as to not distally extend to cover the distal slip interface bushing 904 and the portion of the cantilever beam portion 906 that includes the transverse force sensors 914. The distal slip interface bushing 904 can be constructed the same as or similar to the distal slip interface bushing 604 described above. For example, during sliding motion of the inner tube (not shown) within the outer tube 910, the distal slip interface bushing 904 provides a low friction slip interface between a distal portion of an inner surface of the outer tube 910 and a distal portion of an outer surface of the inner tube. In some embodiments, the slip interface bushing 904 includes an inner perimeter fixedly coupled to an outer surface of the inner tube and includes an outer perimeter that defines a slip interface in slidable contact with the inner surface of the outer tube 910. In some embodiments, the distal slip interface bushing 904 has a bushing inner surface that is fixedly coupled to the outer surface of the inner tube and a bushing outer surface that is chamfered and forms a slip interface with the inner surface of the outer tube 910. The low friction outer slip interface surface of the distal slip interface bushing 904 isolates the inner tube from axial-direction outer tube friction forces as described above. A flexible coupling (not shown) that seals a gap between the outer tube 910 and an end effector/wrist 952/954 assembly is not shown so as to simplify the drawing and explanation. The coupling prevents contaminants from entering the gap during surgery.

Figure 9A:
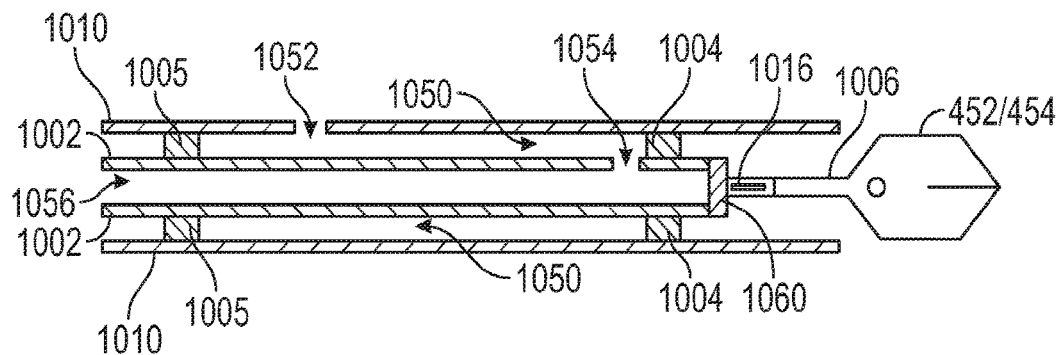
FIG. 9A is an illustrative diagrammatic cross-sectional of a surgical instrument in a medical procedure configuration with the outer tube extended.
Figure 9B:
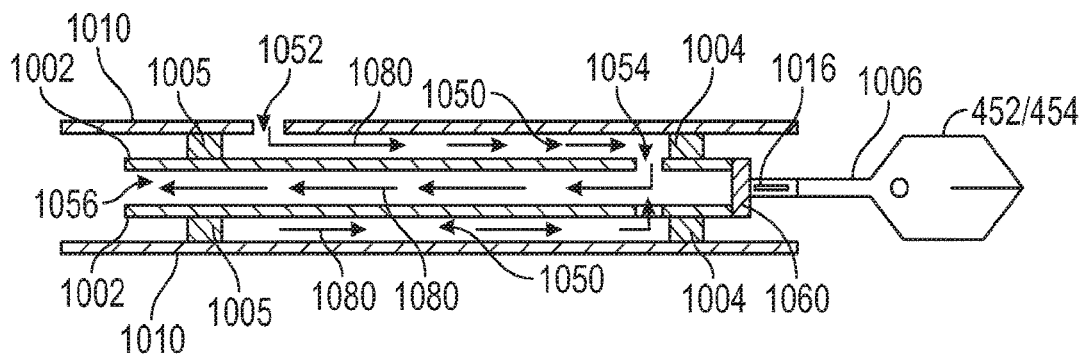
FIG. 9B is an illustrative diagrammatic cross-sectional of a surgical instrument showing example fluid flow in a first example cleaning configuration.
Figure 9C:
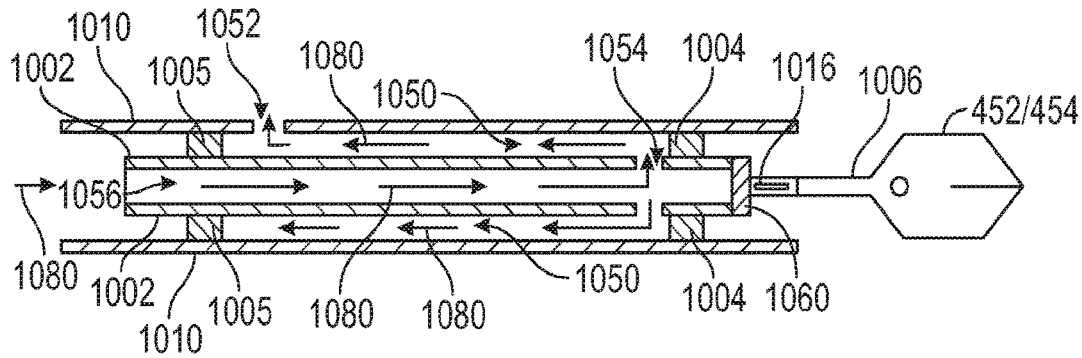
FIG. 9C is an illustrative diagrammatic cross-sectional of a surgical instrument showing example fluid flow in a second example cleaning configuration.

FIG. 9A is an illustrative simplified side cross-sectional diagrammatic view of a surgical instrument in a surgical procedure configuration with the outer tube 1010 extended distally. FIG. 9B is an illustrative simplified side cross-sectional diagrammatic view of a surgical instrument in a first example cleaning configuration with the outer tube retracted proximally, showing cleaning fluid injected to an annulus region between the inner tube 1002 and the outer tube 1010. FIG. 9C is an illustrative simplified side cross-sectional diagrammatic view of a surgical instrument in a second example cleaning configuration with the outer tube 1010 retracted proximally, showing cleaning fluid injected into the inner tube 1002.

Referring to both FIGS. 9B and 9C, in both the first and second example cleaning configurations, the outer tube 1010 is in a proximally retracted position relative to the inner tube 1002 to expose the proximal portion of a cantilever beam portion 1006 and the transverse force sensors 1016 on the cantilever beam portion 1006 for cleaning. The outer tube 1010 and the inner tube 1002, which extends coaxially within the outer tube 1010, together define an annulus region 1050 between an inner surface of the outer tube 1010 and an outer surface of the inner tube 1002. A first proximal fluid port opening 1052 at a proximal portion of the outer tube 1010 provides a fluid flow path between the annulus region 1050 and an environment external to the surgical instrument (additional proximal fluid port openings 1052 are optional). Multiple distal fluid port openings 1054 (only one is shown) at a distal portion of the inner tube 1002 provide a fluid flow path between the annulus region 1050 and a hollow interior of the inner tube 1002. A second proximal port 1056 at a proximal end of the inner tube provides a fluid flow path between the inner tube 1002 and the external environment. Specifically, the inner tube 1002 proximal end portion is open to allow fluid to exit from the inner tube 1002. A baffle wall 1060 blocks the distal end of the inner tube 1002. A distal interface bushing 1004 is positioned distal of the distal fluid port openings 1054. A proximal slip interface bushing 1005 is positioned proximal of the first proximal fluid port opening 1052.

Referring to FIG. 9B, during cleaning of the surgical instrument in the first example cleaning configuration, cleaning fluid is injected through the first proximal fluid port opening 1052 into the annulus region 1050 along a flow path 1080. The cleaning fluid may include mild alkaline cleaners, for example. The cleaning fluid passes inbound, in a distal direction, within the annular region 1050, from an annular region proximal portion to an annular region distal portion. The proximal bushing 1005 blocks fluid from flowing proximally beyond it within the annulus region 1050, which causes the fluid to flow in the distal direction within the annulus region 1050. The distal bushing 1004 blocks fluid from flowing distally past the distal bushing 1004 within the annulus region 1050 and redirects the fluid to flow through the distal fluid port openings 1054 and to flow outbound, in a proximal direction, within a fluid passage defined by the hollow interior of the inner tube 1002. The fluid then flows along fluid flow path 1080 out the second proximal port 1056 at the open end of the inner tube 1002. Thus, a flow of cleaning fluid flushes out the annulus region 1050 and the interior of the inner tube 1002. The provision of a distal fluid flow direction within the annulus region 1050 that is separate from a proximal fluid flow direction within the inner tube 1002 eliminates the need for a separate flush fluid tube within either the inner tube 1002 or within the annulus region to carry cleaning fluid to the inner distal ends of the inner and outer tubes 1002, 1010 (creating more room in the inner tube 1002 for sensor cables that carry the sensed force signal from the transverse force sensors to the surgical system) while still allowing for complete and effective cleaning of inner volumes of the inner and outer tubes 1002, 1010. Moreover, the changing of fluid flow direction at the distal portion of the inner tube 1002 causes cleaning fluid agitation that can enhance cleaning action. Also, as explained below, the proximal retraction of the outer tube 1010 exposes the cantilever beam portion 1006 and the transverse force sensors 1016 so that they can be cleaned through direct application of cleaning fluid.

Referring to FIG. 9C, during cleaning of the surgical instrument in the second example configuration, cleaning fluid is injected through the second proximal fluid port 1056 opening at the proximal end of the inner tube 1002 and flows along a fluid flow path 1080. The cleaning fluid passes inbound, in a distal direction, within the inner tube 1002, from the inner tube proximal portion to the inner tube distal portion. A baffle wall 1060 at the distal end of the inner tube 1002 redirects the cleaning fluid to flow through the distal fluid port openings 1054 and to flow outbound, in a proximal direction, within the annulus region 1050. The distal bushing 1004 also contributes to redirecting the fluid flow to the proximal direction within annulus region 1050 by blocking distal direction fluid flow beyond the distal bushing 1004. The cleaning fluid then flows out the first proximal port 1052. The proximal bushing 1005 blocks cleaning fluid from flowing beyond the proximal bushing 1005 in the proximal direction within the annulus region to redirect the fluid to flow through the first proximal fluid port 1052 as shown by the fluid flow path 1080. Thus, as with the first cleaning configuration, the cleaning fluid flushes out the annulus region 1050 and the interior of the inner tube 1002. Change in fluid flow direction at the distal portion of the inner tube 1002 causes fluid agitation that can enhance cleaning action due to the fluid flow.

Figure 10:
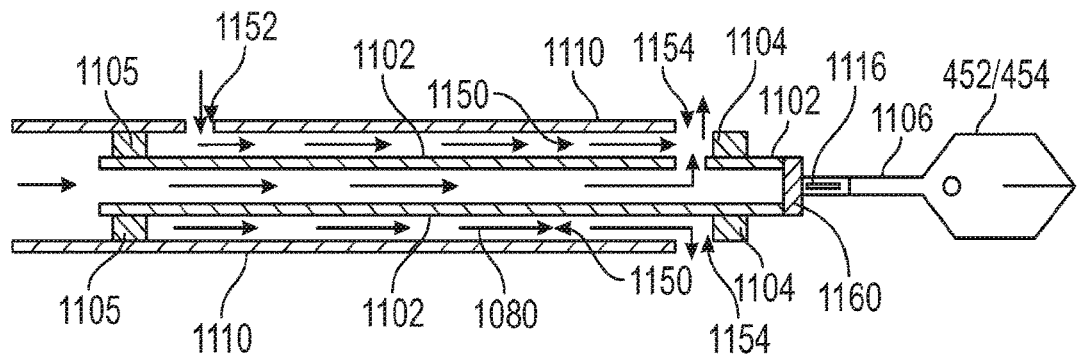
FIG. 10 is an illustrative diagrammatic cross-sectional view of a surgical tool showing example fluid flow in a third example cleaning configuration.

FIG. 10 is an illustrative simplified side cross-sectional diagrammatic view of another surgical instrument shown in a third example cleaning configuration. In this example configuration, an outer tube 1110 is retracted proximally, showing cleaning fluid flow path 1080 in both the annulus region 1050 and to the inner tube 1102 and flowing inbound, in a distal direction, within each of these passages and out at a distal portion of the inner tube 1102 and at a distal portion of the annulus region 1150. More particularly, in the third example cleaning configuration, the outer tube 1110 is retracted in a proximal direction far enough relative to the inner tube 1102 so that a distal end of the outer tube 1110 does not reach the distal slip interface bushing 1104. Cleaning fluid is injected through a first proximal fluid port opening 1152 and through a second proximal port opening 1156 so that fluid flows distally within an annulus region 1150 and flows distally within the inner tube 1102. A proximal slip interface bushing 1105 blocks fluid flow beyond the proximal slip interface bushing 1105 (in a proximal direction) within the annulus region 1150, which directs fluid to flow in a distal direction within the annulus region. Fluid flowing within the annulus region 1152 flows out at the distal end of the outer tube 1110 as shown by fluid flow path 1080. Fluid flowing distally within the inner tube 1102 flows out through a distal port opening 1154. This example embodiment maximizes flow through the annulus for a given driving fluid pressure. The inner tube 1102 can be further cleaned through utilizing a flush tube (not shown) inserted into the inner tube 1102 to direct cleaning fluid through the center of the inner tube 1102. As with the first and second cleaning configurations, the outer tube 1110 is retracted far enough to expose the cantilever beam portion 1106 and the transverse force sensors 1116 thereon so that they can be cleaned through direct application of cleaning fluid.

The distal slip interface bushings 1004 and 1104, and the proximal slip interface bushings 1005 and 1105 described above can be constructed the same as or similar to the distal slip interface bushing 604 and the proximal slip interface bushing 605 described above. For example, during sliding motion of the inner tubes 1002, 1102 within the outer tubes 1010, 1110, the slip interface bushings 1004, 1104 and 1005, 1105 provide a low friction slip interface between a portion of an inner surface of the outer tubes 1010, 1110 and a portion of an outer surface of the inner tubes 1002, 1102. In some embodiments, the slip interface bushings 1004, 1104 and 1005, 1105 have a bushing inner surface that is fixedly coupled to the outer surface of the inner tubes 1002, 1102 and a bushing outer surface that is chamfered and forms a slip interface with the inner surface of the outer tubes 1010, 1110. In some embodiments, the distal slip interface bushings 1004, 1104 and 1005, 1105 include an inner perimeter fixedly coupled to an outer surface of the inner tubes 1002, 1102 and include an outer perimeter that defines a slip interface in slidable contact with the inner surface of the outer tubes 1010, 1110. The low friction outer slip interface surfaces of the slip interface bushings 1004, 1104 and 1005, 1105 isolate the inner tubes 1002, 1102 from axial-direction outer tube friction forces as described above.

Figure 11A:
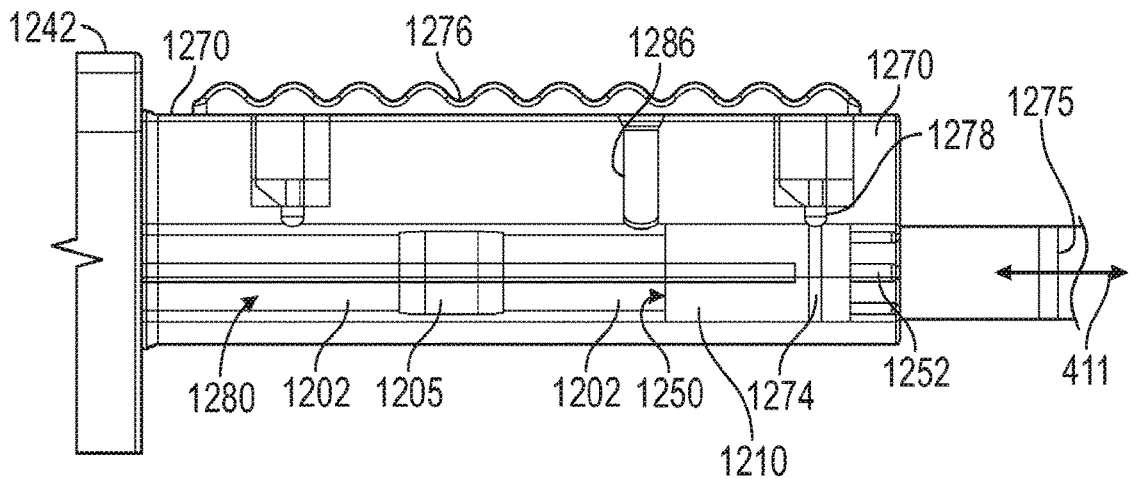
FIGS. 11A-11B are illustrative side cross-section views of portion of a surgical instrument including an inner tube, an outer tube, and a handle with the outer tube in an extended position (FIG. 11A) and a retracted position (FIG. 11B).
Figure 11B:
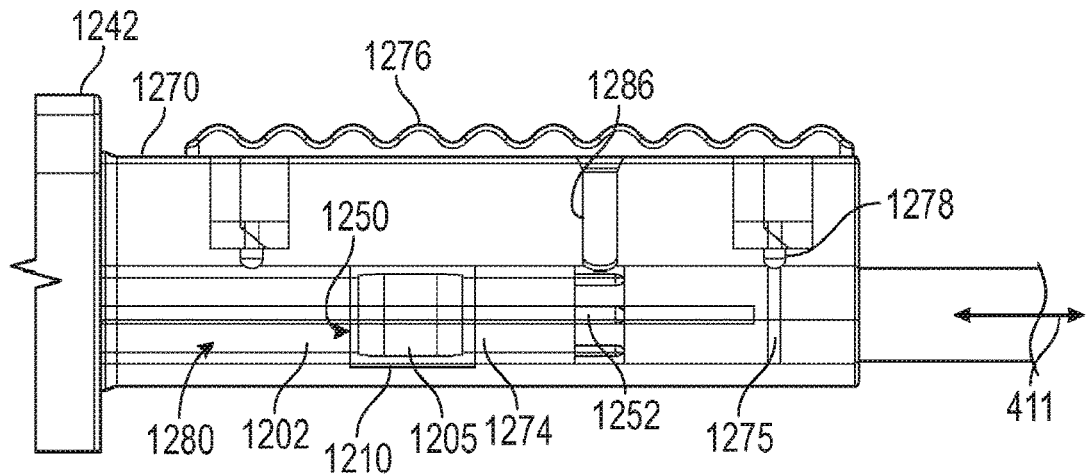

FIGS. 11A-11B are illustrative side cross-section views of a portion of a surgical instrument including an inner tube 1202, an outer tube 1210, and a handle 1270. The handle 1270 is coupled to the chassis 1242 of the surgical instrument and defines an elongated handle channel 1280, in which the outer and inner tubes 1210, 1202 are received in a coaxial nested configuration. The outer tube 1210 is slidable relative to the inner tube 1202 within the handle channel 1280 between an extended distal position and a retracted proximal position.

FIG. 11A shows the outer tube 1210 in the extended position. FIG. 11B shows the outer tube 1210 in the retracted position. A proximal locking groove 1274 is defined in an outer surface of outer tube 1210, and used for locking the outer tube 1210 in the extended position, for example during a medical procedure. Similarly, a distal locking groove 1275 is defined in the outer surface of outer tube 1210, and used for locking the outer tube 1210 in the retracted position, during cleaning for example. More particularly, the first handle 1270 includes a spring-mounted bearing 1278 sized and biased to insert within proximal groove 1274 so that the bearing 1278 and the groove 1274 interlock and lock the outer tube 1210 in a distally extended position during a medical procedure. The spring-mounted bearing 1278 is also sized and biased to insert within distal groove 1275 so that the bearing 1278 and the groove 1275 interlock so as to lock the outer tube 1210 in a proximally retracted position during cleaning. A user-operable locking mechanism 1276 is used to selectively retract the bearing 1278 away from the outer tube 1210, and out of either proximal groove 1274 or distal groove 1275, to allow the outer tube 1210 to slidably move within the handle channel 1280 between the extended and retracted positions.

Still referring to FIGS. 11A-11B, the first handle 1270 includes an external cleaning fluid flush port 1286 that provides cleaning fluid access between the handle channel 1280 and an environment external to the surgical instrument. The external flush port 1286 aligns with a first proximal port 1252 in the outer tube 1210 when the outer tube 1210 is in the retracted position so as to permit cleaning fluid injection to an annulus region 1250 between the inner and outer tubes 1202, 1210. FIG. 11B further shows a proximal end portion of outer tube 1210 covering proximal bearing 1205 when the outer tube 1210 is in the retracted position. The proximal end portion of the outer tube 1210 is shown transparent to show the proximal bearing 1205 inside.

Figure 11C:
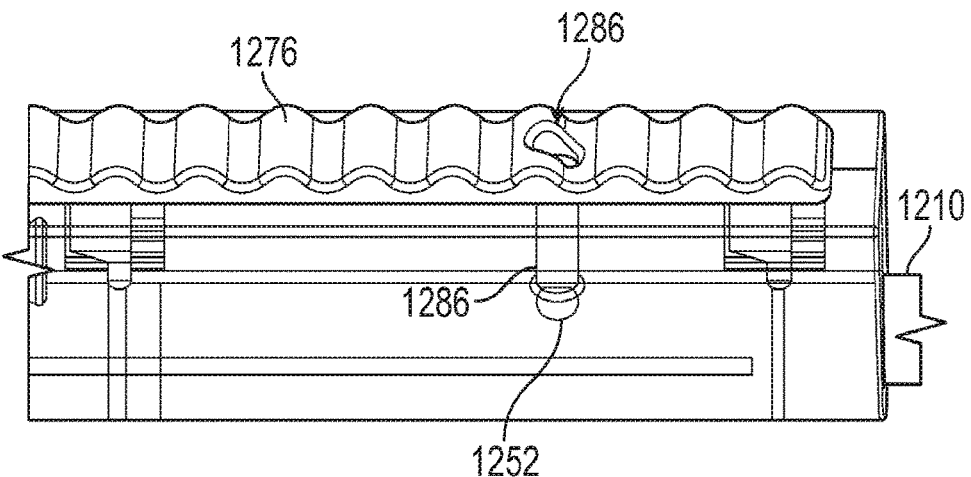
FIG. 11C is a partially cut-away perspective view of a portion of the first handle and the outer tube of FIGS. 11A-11B, with the outer tube in the retracted position and an external flush port aligned with the first proximal port opening.

FIG. 11C is a partially cut-away perspective view of a portion of the first handle 1270 and the outer tube 1210, with the outer tube in the retracted position and the external flush port 1286 aligned with the first proximal port opening 1252. It is noted that with the outer tube 1210 in the extended position, the proximal end of the outer tube 1210 is distally displaced from the proximal bushing 1205, but with the outer tube 1210 in the retracted position, the proximal end of the outer tube 1210 extends over the proximal bushing 1205.

Figure 12A:
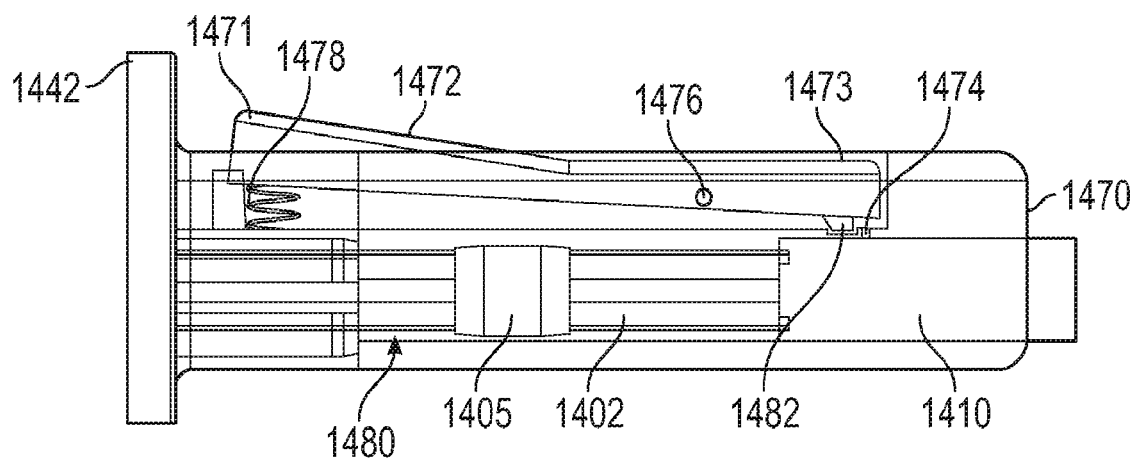
FIGS. 12A-12B are illustrative side cross-section views of portion of a surgical instrument including an inner tube, an outer tube, and a second handle with the outer tube in an extended position (FIG. 12A) and a retracted position (FIG. 12B).
Figure 12B:
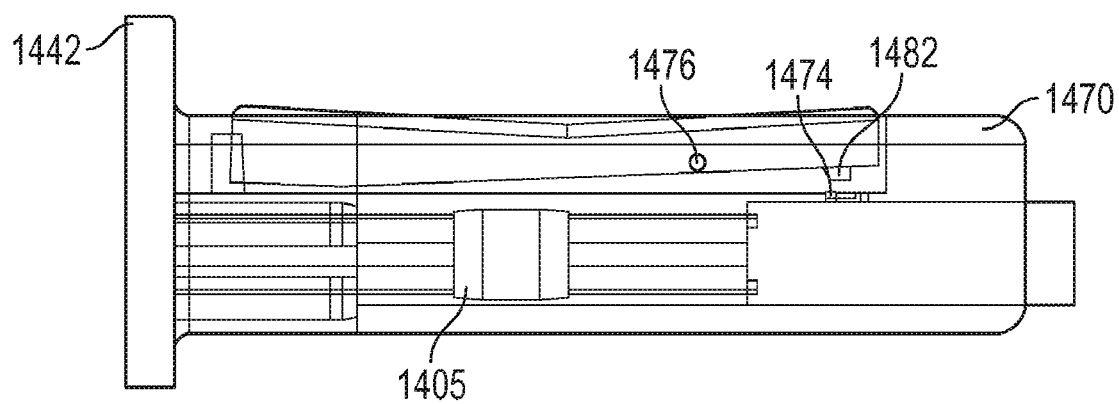

FIGS. 12A-12B are illustrative side cross-sectional views of a portion of a surgical instrument showing interior details including an inner tube 1402, an outer tube 1410, and an alternative handle 1470. The handle 1470 is coupled to a chassis 1442 of the surgical instrument and defines an elongated channel 1480 in which the outer and inner tubes 1410, 1402 are received in a coaxial nested configuration. The outer tube 1410 is slidable relative to the inner tube 1402 within the handle channel 1480, and it is also slidable relative to chassis 1442, between the extended distal position as shown in FIG. 12A and the retracted proximal position as shown in FIG. 12B.

The handle 1470 includes a user-operated external locking mechanism 1472 coupled to selectively lock the outer tube 1410 in the extended position. A pin 1474 projects outward from an outer surface of a proximal portion the outer tube 1410. The pin 1474 is received within an interior groove (not shown) formed on an interior surface of locking mechanism 1472. The pin 1474 slides within the interior groove as the outer tube 1410 moves between the extended and retracted positions.

The locking mechanism 1472 is pivotally mounted within handle 1470 at a pivot fulcrum 1476. A proximal spring 1478 is coupled to a proximal portion 1471 of the locking mechanism 1472 (FIG. 12A) to rotationally urge a distal portion 1473 of the locking mechanism 1472 toward the outer tube 1410. A blocking pin 1482 (FIG. 12B) extends from the distal portion 1473 of the locking mechanism 1472 toward the outer tube 1410. The blocking pin 1482 is positioned to interlock with the counterpart receiving pin 1474 when the outer tube 1410 is in the distally extended position so as to lock the outer tube 1410 in the distally extended position during a medical procedure. A user application of force at the proximal end 1471 of the locking mechanism 1472 compresses the spring 1478 and causes pivoting of the blocking pin 1482 away from the outer tube 1410 and away from the receiving pin 1474 to permit retraction of the outer tube 1410.

Figure 12C:
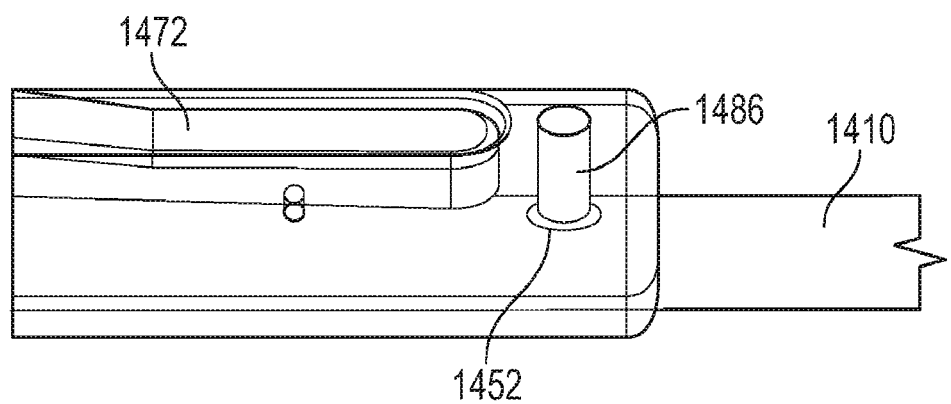
FIG. 12C is an illustrative partially transparent view of a portion of the second handle of FIGS. 12A-12B showing that in the retracted position, an external fluid flush port is aligned with a first proximal port formed in the outer tube.

FIG. 12C is an illustrative partially transparent view of a portion of the handle 1470 showing that in the retracted position, an external cleaning fluid flush port 1486 aligned with a first proximal port 1452 in the outer tube 1410. Thus cleaning fluid may be introduced within the outer and inner tubes 1410 and 1402 as described above.

Figure 13A:
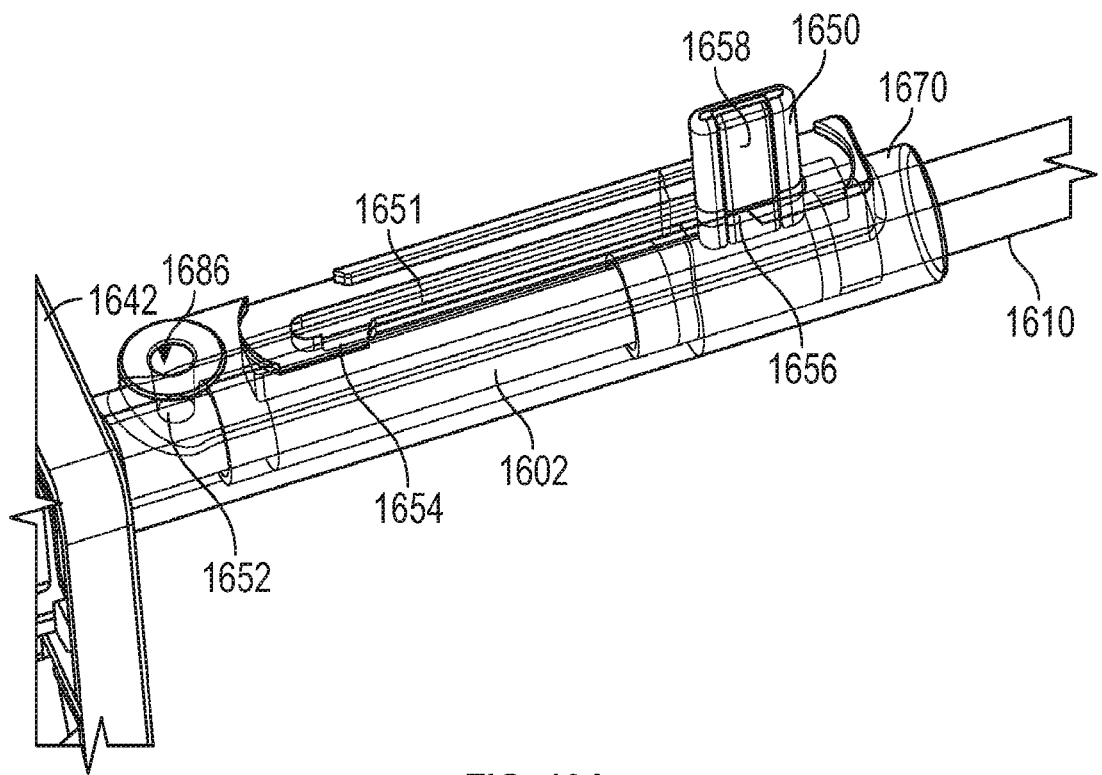
FIGS. 13A-13B are illustrative partially transparent perspective views showing interior details including an inner tube, an outer tube, and third handle with the outer tube in an extended position (FIG. 13A) and a retracted position (FIG. 13B).
Figure 13B:
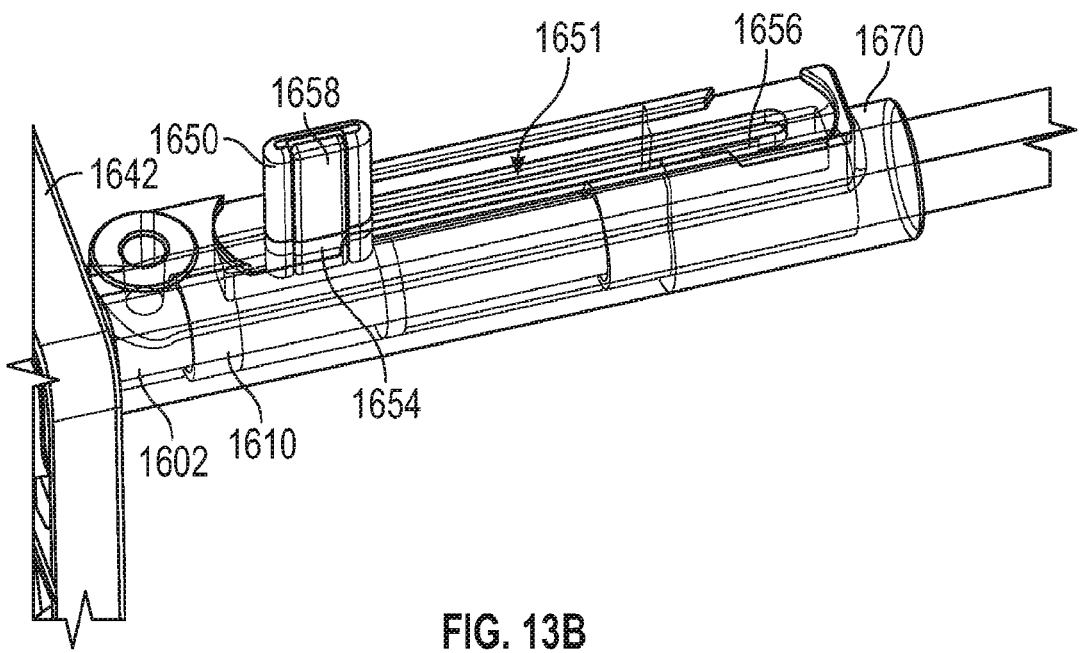

FIGS. 13A-13B are illustrative partially transparent perspective views of a portion of a surgical instrument showing an inner tube 1602, an outer tube 1610, a proximal chassis 1642 and an alternative handle 1670 of a surgical instrument with the outer tube 1610 in an extended position (FIG. 13A) and a retracted position (FIG. 13B). To simplify the explanation, portions of the handle 1670 that are similar to those of the handles 1270, 1470 are not described. A tab 1650 is included in a proximal portion of the outer tube 1610. An axially extending slot opening 1651 in the handle 1670 is sized to slidably receive tab 1650. Tab 1650 travels within the slot 1651 during axial movement of the outer tube 1610 between the extended and retracted positions. The slot 1651 includes a proximal cutout 1654 and a distal cutout 1656, which are both defined in the perimeter of slot 1651. A resilient locking feature 1658 is coupled to tab 1650 and is spring-biased to be urged outwardly from the tab 1650 toward the perimeter of slot 1651, and locking feature 1658 is sized for a close interlocking fit within each of the cutout areas 1654, 1656. The cutouts 1654, 1656 are positioned along slot 1651 so that when the outer tube 1610 is in the extended position, locking feature 1658 is urged to move to insert within distal cutout 1654, and when the outer tube 1610 is in the retracted position, locking feature 1658 is urged to move to insert within the proximal cutout 1651. A user applies an inward force upon the locking feature 1658 (i.e., against its outward spring bias) to press it flush against the tab 1650, which enables the user to slide tab 1650 within the slot 1651 to move the outer tube 1610 between extended and retracted positions. Thus locking feature 1658 in tab 1650 holds outer tube 1610 in the desired extended or retracted position. In one optional aspect, the proximal cutout 1654 is not used, and only the distal cutout 1656 is used to lock the shaft in the desired extended position. With the outer tube 1610 in the retracted position, an external fluid flush port 1686 in handle 1670 is aligned with a first proximal port 1652 in the outer tube 1610, and cleaning may be conducted as described above.

Figure 14A:
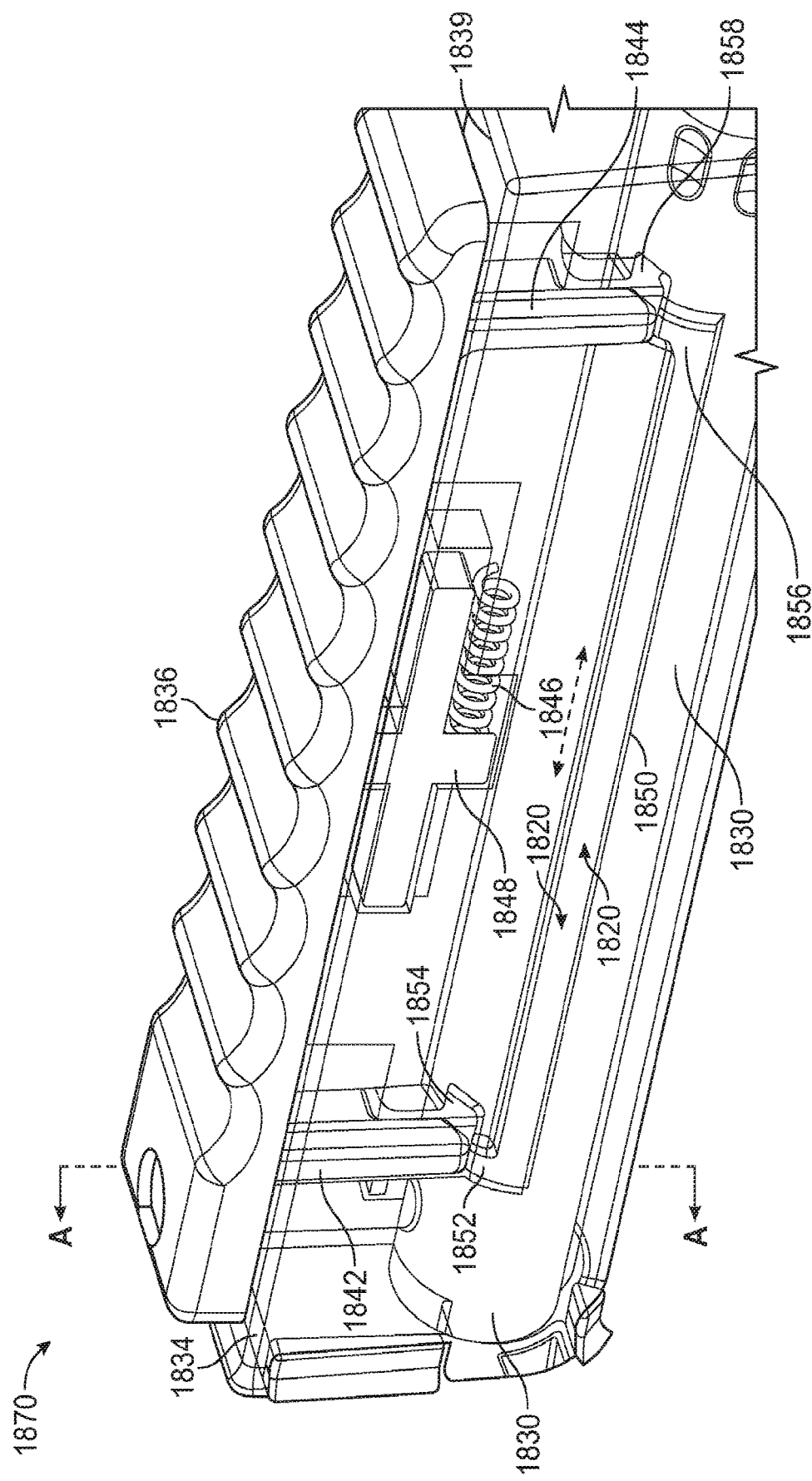
FIG. 14A is an illustrative partially transparent perspective view of an example handle.
Figure 14B:
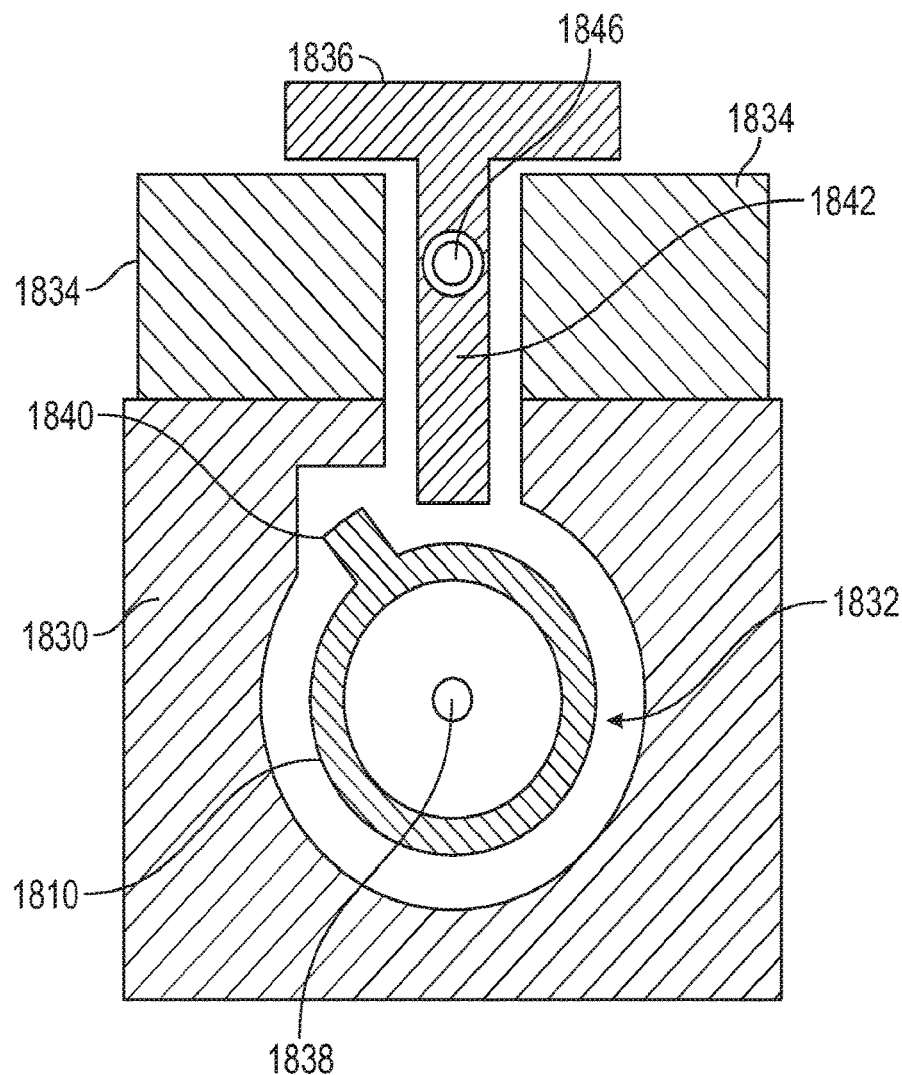
FIG. 14B is an illustrative cross-section view of the example handle of along A-A of FIG. 14A.
Figure 14C:
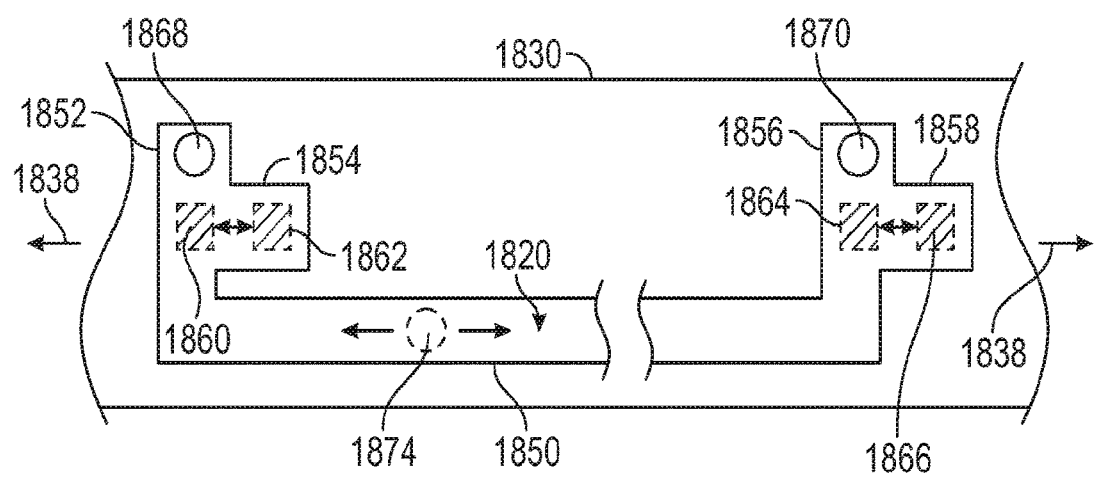
FIG. 14C is an illustrative drawing showing a groove formed within a mounting block portion of the handle of FIGS. 14A-14B.

FIG. 14A is an illustrative partially transparent perspective view of an alternative handle 1870. FIG. 14B is an illustrative cross-section view of the handle 1870 taken along line A-A of FIG. 14A. FIG. 14C is an illustrative drawing showing a groove 1820 formed within a mounting block portion 1830 of the handle 1870.

Referring to FIGS. 14A-14B, the handle 1870 includes the mounting block portion 1830 that defines an inner bore 1832 (FIG. 14B) into which an outer tube 1810 (FIG. 14B) is slidably inserted, A proximal portion of an inner tube (not shown) also can be inserted within the outer tube 1810. A support structure 1834 is integrally formed with and upstands from the mounting block 1830. A slider 1836 is slidably mounted to the support structure 1834 for movement in a direction parallel to a shared center axis 1838 (FIGS. 14A and 14C) of the inner bore 1832 and the outer tube 1810. A guide pin 1840 (FIG. 14B) upstands outwardly from the outer tube 1810 and extends within the groove 1820 formed in the mounting block 1830. Proximal and distal blocking posts 1842, 1844 extend inwardly from the slider 1836 into respective proximal and distal portions of the groove 1820 described more fully below with reference to FIG. 14C. A spring 1846 is attached by a fixture 1848 to the slider 1836 and biased to urge the proximal and distal posts 1842, 1844, which extend from the slider 1836, to respective proximal and distal blocking positions within the slot 1820. For example, a user can impart a force to the slider 1836 to counter the spring force and move the proximal and distal posts 1842, 1844 to respective proximal and distal unblocking positions within the slot 1820.

Referring to FIG. 14C, the groove 1820 includes an elongated groove portion 1850 that extends in a direction parallel to the shared center axis 1838 of the outer tube 1810 and the inner bore 1832. The groove 1820 also includes a proximal circumferential groove portion 1852 that extends in a circumferential direction and includes a proximal unblocking notch portion 1854 that extends distally from a center portion of the proximal circumferential groove 1852. The groove 1820 also includes a distal circumferential groove portion 1856 that extends in a circumferential direction and includes a distal unblocking notch portion 1858 that extends distally from a center portion of the distal circumferential groove 1856.

Referring to FIGS. 14A and 14C, the proximal blocking post 1842 is moveable between a proximal blocking position 1860 (indicated by dashed lines) that is within the proximal circumferential groove portion 1852 outside the proximal notch 1854 and a proximal unblocking position 1862 (indicated by dashed lines) that is within the proximal notch 1854. Similarly, the distal blocking post 1844 is moveable between a distal blocking position 1864 (indicated by dashed lines) that is within the distal circumferential groove portion 1856 outside the distal notch 1858 and a distal unblocking position 1866 (indicated by dashed lines) that is within the distal notch 1858.

The spring 1846 is biased to urge the proximal and distal blocking posts 1842, 1844 into the respective proximal and distal blocking positions 1860, 1864. When the outer tube 1810 is retracted, the guide pin 1840 is located in a proximal locked position 1868 within the proximal circumferential groove 1852 with the proximal blocking post 1842 in the proximal locking position 1860 to block passage of the guide pin 1840 to the elongated groove portion 1850. When the outer tube 1810 is extended, the guide pin 1840 is located in a distal locked position 1870 within the distal circumferential groove 1856 with the distal blocking post 1844 in the distal blocking position 1864 to block passage of the guide pin 1840 to the elongated groove portion 1850.

To move the outer tube 1810 from the retracted to the extended position, a user imparts a force to the slider 1836 to overcome the spring force and move the slider 1836 and the respective proximal and distal blocking posts 1842,1844 connected thereto to the respective proximal and distal unblocking positions 1862, 1866. The user rotates the outer tube 1840 about the center axis 1838 so that the guide pin 1840 slides out of the proximal circumferential groove 1852 and into the elongated groove 1850. The user next imparts a distal direction force to extend the outer tube 1810 from within the bore 1832 causing the guide pin 1840 to move in a distal direction within the elongated groove 1850 as shown at 1874. The user next rotates the outer tube 1810 so that the guide pin 1840 slides into the distal circumferential groove 1856, past the distal blocking post 1844, which is located in the distal unblocking position 1866, to the distal locked position 1870. The user releases the slider 1836 so that the spring 1846 imparts a force to urge the distal blocking post 1844 to the distal blocking position 1864 to lock the guide pin 1840 within the distal circumferential groove 1856 at the distal locked position 1870. It will be appreciated that when the user releases the slider 1836, the proximal blocking post 1842 moves to the proximal blocking position 1862.

Conversely, to move the outer tube 1810 from the extended to the retracted position, a user imparts a force to the slider 1836 to overcome the spring force and move the respective proximal and distal blocking posts 1842, 1844 connected thereto to respective proximal and distal unblocking positions 1854, 1856. The user rotates the outer tube about the center axis 1838 so that the guide pin 1840 slides out of the distal circumferential groove 1856 and into the elongated groove 1850. The user next imparts a proximal direction force to retract the outer tube 1810 into the bore 1832 causing the guide pin 1840 to move in a proximal direction within the elongated groove 1850 as shown at 1874. The user next rotates the outer tube 1810 so that the guide pin 1840 slides into the proximal circumferential groove 1852, past the retracted proximal blocking post 1842, to the proximal locked position 1868. The user releases the slider 1836 so that the spring 1846 imparts a force to urge the proximal blocking post 1842 into the proximal blocking position 1860 to lock the guide pin 1840 at the proximal locked position 1868. It will be appreciated that when the user releases the slider 1836, the distal blocking post 1844 moves into the distal blocking position 1864.

Figure 15C:
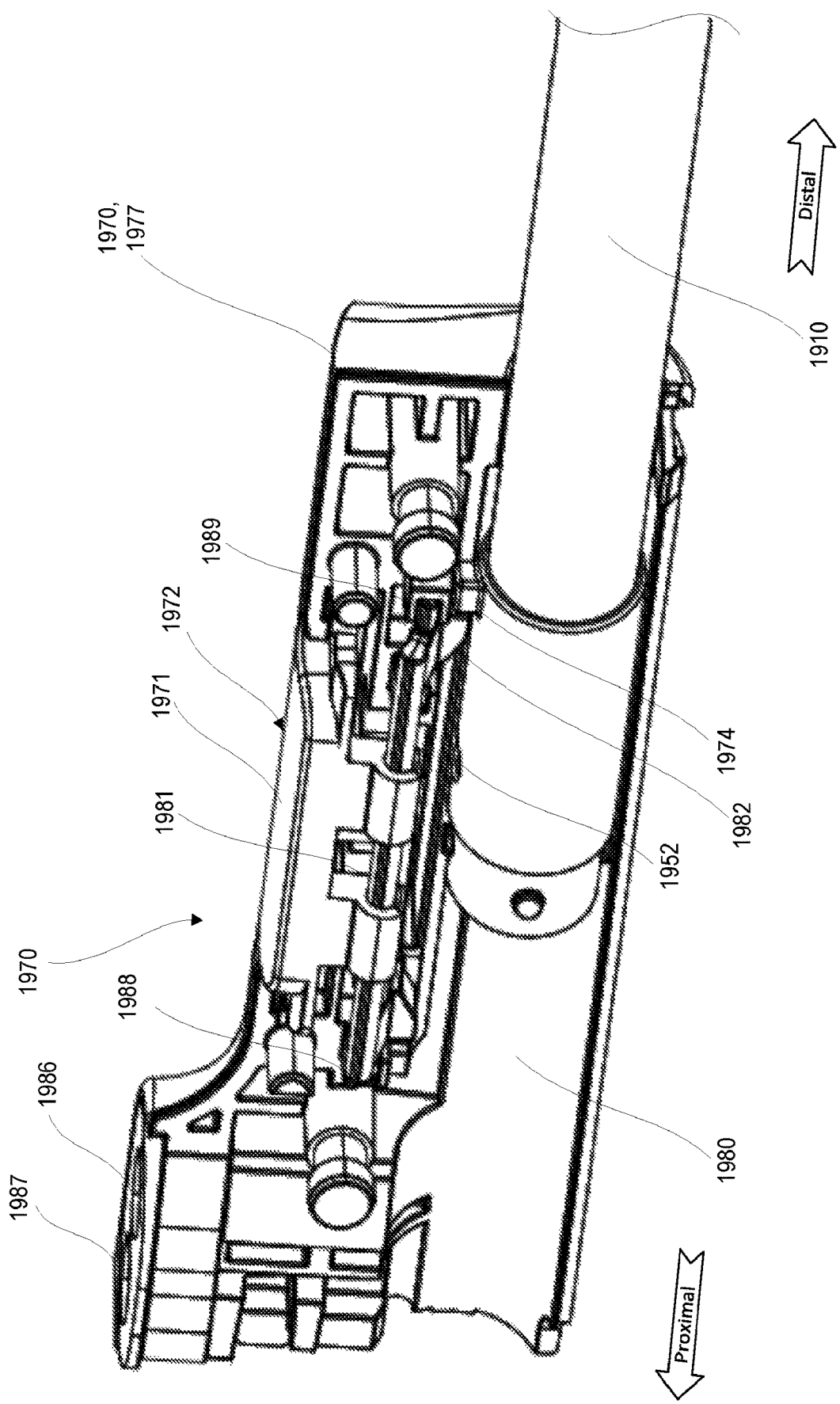
FIG. 15C is a perspective view of a portion of the surgical instrument of FIG. 15A with a portion of the housing of the handle removed for illustration purposes and the outer tube shown in a distally extended position.
Figure 15D:
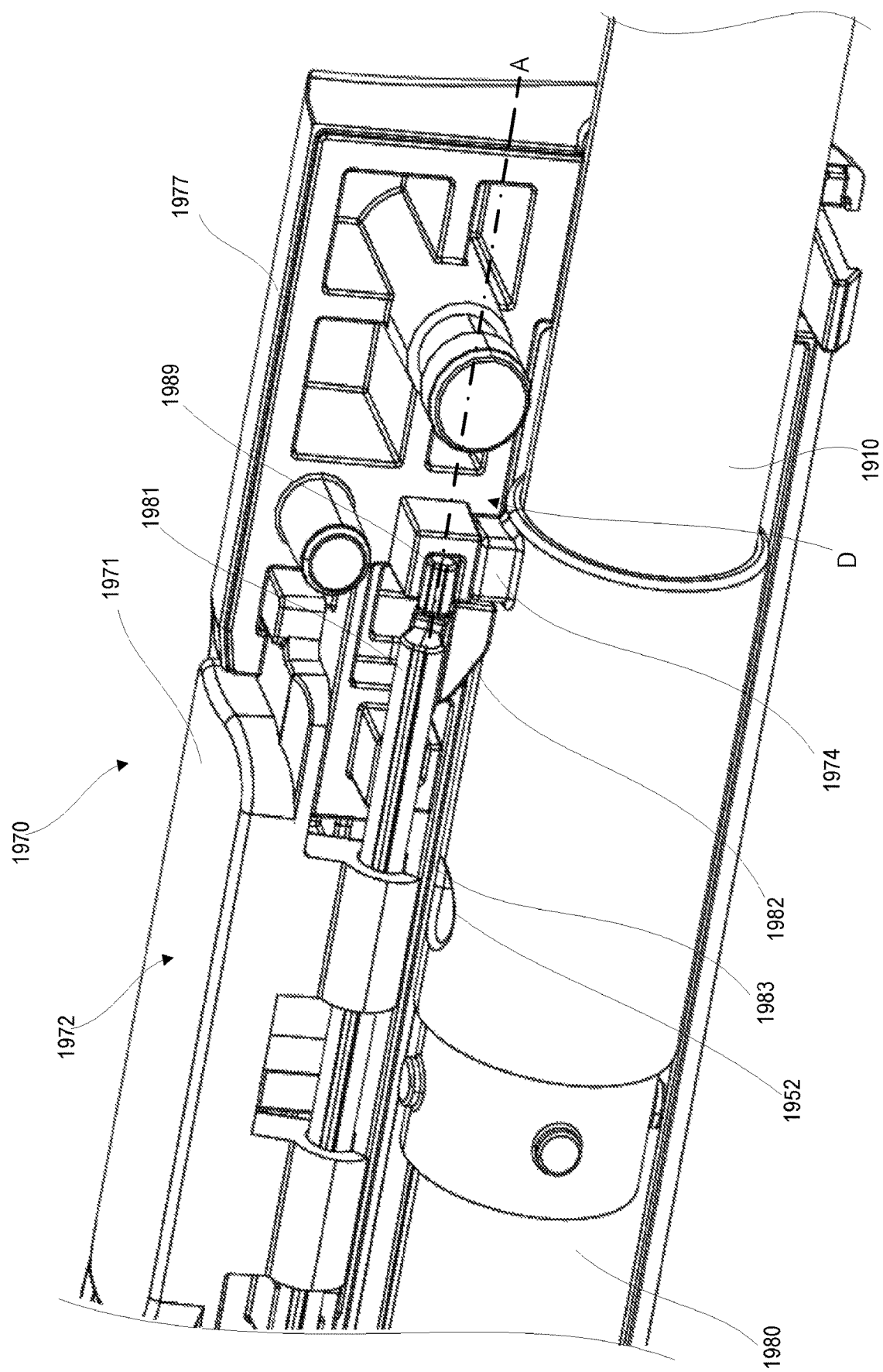
FIG. 15D is an enlarged perspective view of a portion of the surgical instrument of FIG. 15A with a portion of the housing of the handle removed for illustration purposes and the outer tube in a distally extended position.

FIGS. 15A-15F illustrate various views of a surgical instrument 1926. The surgical instrument 1926 includes a proximal chassis (not shown), a handle 1970, an outer tube 1910 and an inner tube 1902. The handle 1970 is coupled to the proximal chassis of the surgical instrument 1926 and defines an elongated handle channel 1980 in which the outer and inner tubes 1910, 1902 are received in a coaxial nested configuration. The outer tube 1910 is slidable relative to the inner tube 1902 within the handle channel 1980, and it is also slidable relative to chassis between a distally extended position as shown in FIGS. 15C and 15D and a proximally retracted position, shown in FIGS. 15E and 15F.

The handle 1970 includes a user-operated locking mechanism 1972 coupled to selectively lock the outer tube 1910 in the distally extended position and or the proximally retracted position. The locking mechanism 1972 includes an external button 1971 operatively coupled to a rotatable rod 1981 having a distal stopper 1982 disposed at a distal end of the rotatable rod 1981 and a proximal stopper 1984 disposed at a proximal end of the rotatable rod 1981. A post 1974 projects outward from an outer surface of a proximal portion the outer tube 1910. The post 1974 is received within an interior channel 1983 (see, e.g., FIG. 15B) formed within an interior of a housing 1977 of the handle 1970. The housing 1977 can be formed by two components coupled together. The post 1974 slides within the interior channel 1983 as the outer tube 1910 moves between the distally extended and the proximally retracted positions as described in more detail below.

The locking mechanism 1972 is pivotally mounted within handle 1970 at a proximal pivot joint 1988 and a distal pivot joint 1989. A pair of springs (not shown) are disposed beneath the button 1971 that bias the button 1971 in an upward direction. With the button 1971 in the biased position, the stoppers 1982 and 1984 are positioned within the interior channel 1983 and together with blocking portions (defining the ends of the interior channel, not shown) of the housing 1977 prevent the outer tube 1910 from being moved distally or proximally. For example, when the two components of the housing 1977 of the handle 1970 are coupled together, a proximal blocking portion (not shown) and a distal blocking portion (not shown) are formed with the distal blocking portion disposed at location D shown in FIG. 15D, and the proximal blocking portion disposed at location P shown in FIG. 15E. Thus, when the outer tube 1910 is in the distally extended position, and the button 1971 is not depressed (e.g., is in the biased position), the post 1974 is trapped between the distal stopper 1982 and the distal blocking portion of the housing 1977. Similarly, when the outer tube 1910 is in the proximally retracted position, and the button 1971 is not depressed (e.g., is in the biased position), the post 1974 is trapped between the proximal stopper 1984 and the proximal blocking portion of the housing 1977.

Figure 15E:
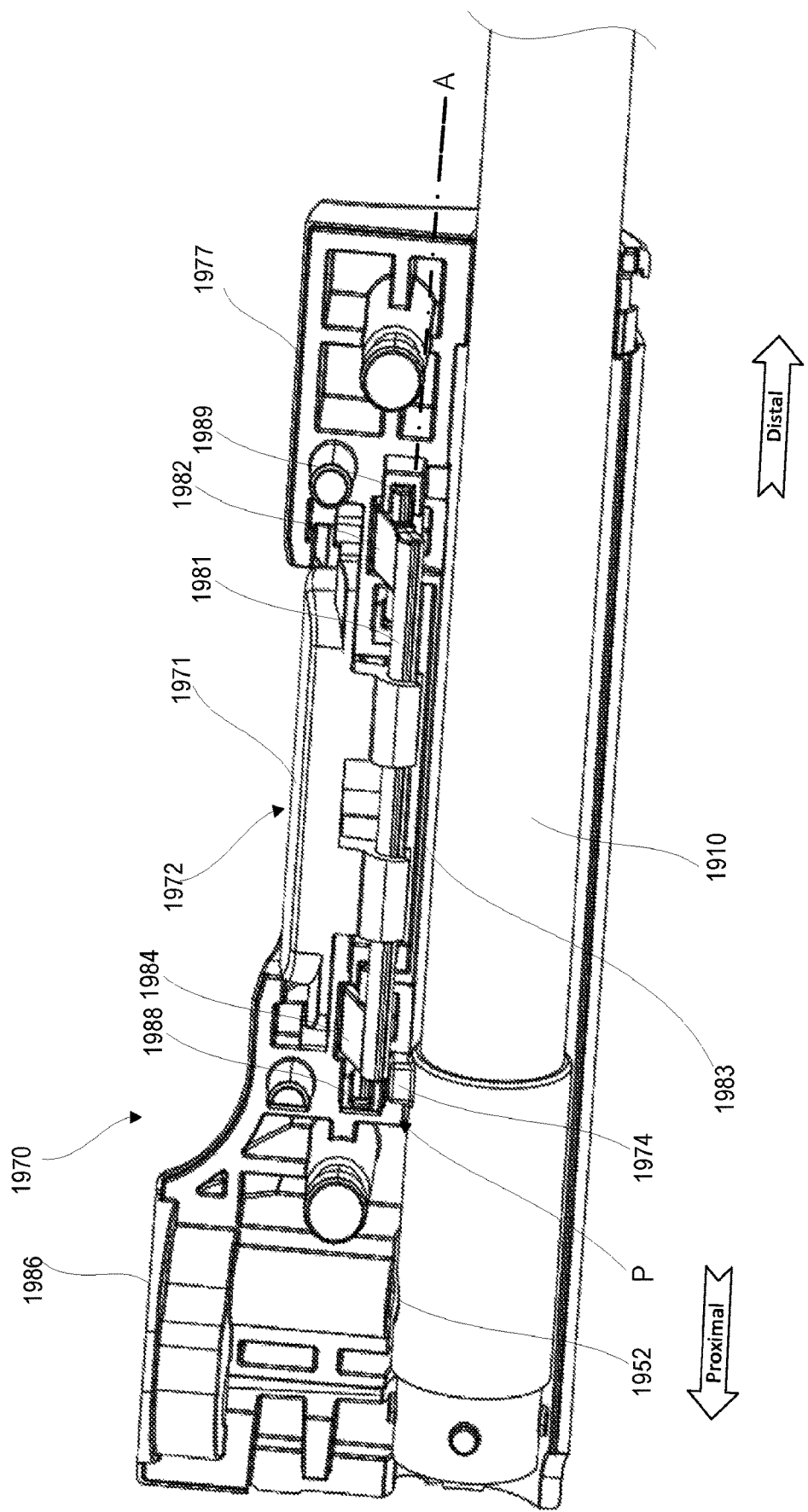
FIG. 15E is a perspective view of a portion of the surgical instrument of FIG. 15A with a portion of the housing of the handle removed for illustration purposes, the outer tube in a proximally retracted position and the button in a depressed position.
Figure 15F:
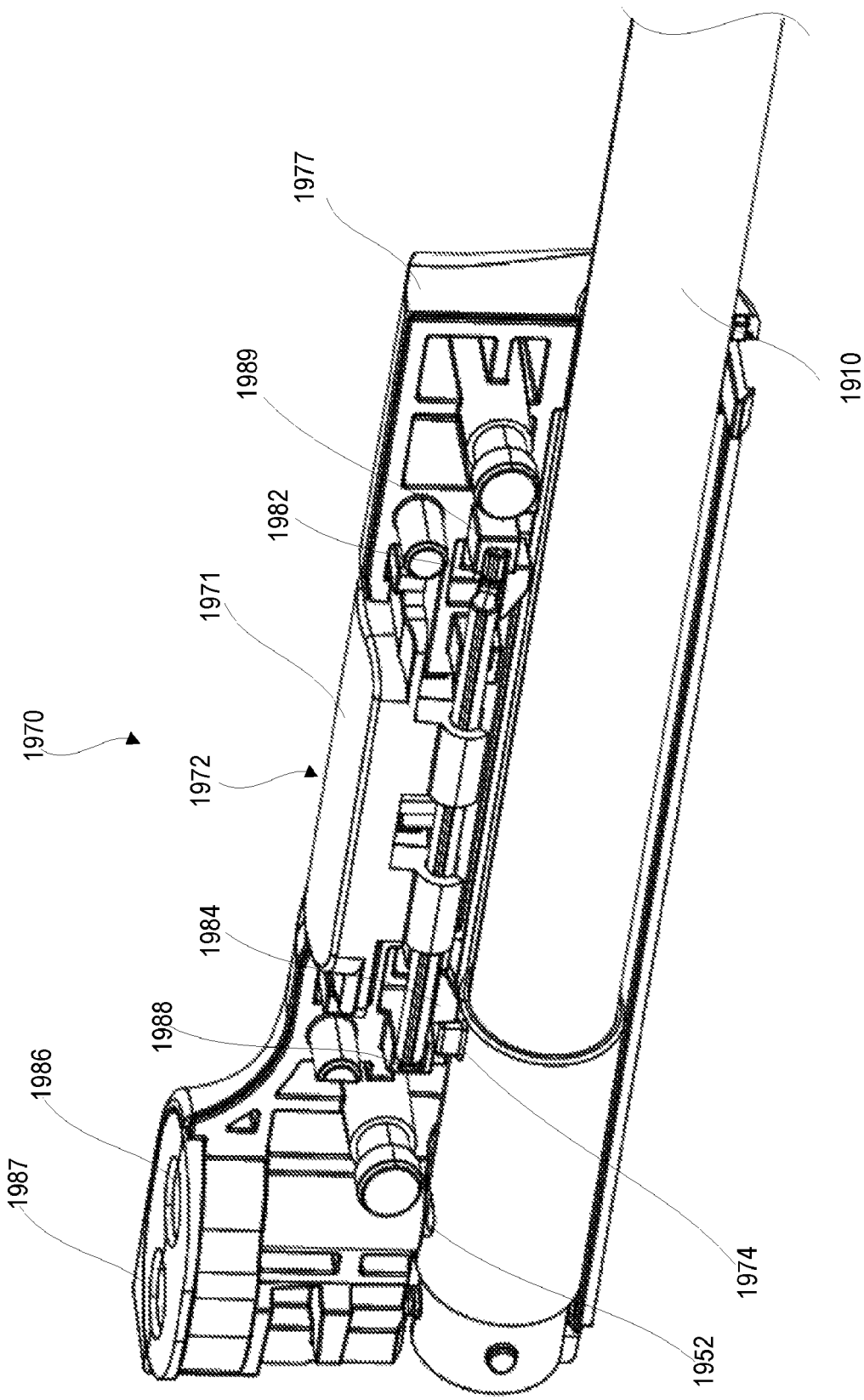
FIG. 15F is a perspective view of a portion of the surgical instrument of FIG. 15A with a portion of the housing of the handle removed for illustration purposes and the outer tube in the proximally retracted position.

To move the outer tube 1910 between the distally extended position and the proximally retracted position, the button 1971 is depressed with sufficient force to overcome the spring force of the springs (not shown) such that the rotatable rod 1981 is rotated about the pivot axis A, and the stoppers 1982 and 1984 are rotated out of the interior channel 1983. This allows the post 1974 to slide within the interior channel 1983, and thus move the outer tube 1910 proximally and distally. FIG. 15E illustrates the button 1971 depressed, the rotatable rod 1981 rotated about the axis A, the stoppers 1982 and 1984 rotated out of the channel 1983, and the outer tube 1910 in the proximally retracted position. FIG. 15F illustrates the outer tube 1910 locked in the proximal position, with the button 1974 released and in the biased upward position, and FIG. 15D illustrates the outer tube 1910 locked in the distal position, with the button 1974 released and in the biased upward position The handle 1970 also defines two fluid ports—a first fluid port 1986 and a second fluid port 1987. The first fluid port 1986 can be used to introduce a fluid into the outer tube 1910 via an outer tube port 1952 to flush and clean the outer tube 1910 and inner tube 1902 as described above for previous embodiments. More specifically, when the outer tube 1910 is in the proximally retracted position, the fluid port 1986 aligns with the outer tube port 1952 and is in fluid communication therewith as shown, for example, in FIG. 15E. The coupling between the fluid port 1986 and the outer tube port 1952 can include a seal (not shown) to prevent leakage of fluid. The second fluid port 1987 can be used to introduce a fluid into the proximal chassis to flush and clean the interior of the proximal chassis.

Persons of skill in the art will understand that the various projections, pins, grooves, slots, spring positions, and the like may optionally be reversed from the structures described above in relation to FIGS. 11A-15F in order to achieve the same mechanical function. For example, an annular groove may be replaced with an annular projection, a projection may be replaced with a slot, a spring in compression may be replaced with a spring in tension, etc. in order to provide the necessary locking of the moveable outer tube in the desired distal or proximal position in relation to the inner tube and to the instrument chassis.

The above description is presented to enable any person skilled in the art to create and use a surgical instrument with nested shafts. In an example surgical instrument with nested shafts, a low friction interface isolates the inner tube from axial friction forces imparted to the outer tube. In an example surgical instrument with nested shafts, an outer tube is retractable to facilitate flushing with cleaning fluid. Various modifications to the examples will be readily apparent to those skilled in the art, and the generic principles defined herein may be applied to other examples and applications without departing from the spirit and scope of the invention. In the preceding description, numerous details are set forth for the purpose of explanation. However, one of ordinary skill in the art will realize that the examples in the disclosure might be practiced without the use of these specific details. In other instances, well-known processes are shown in block diagram form in order not to obscure the description of the invention with unnecessary detail. Thus, the foregoing description and drawings of embodiments in accordance with the present invention are merely illustrative of the principles of the invention. Therefore, it will be understood that various modifications can be made to the embodiments by those skilled in the art without departing from the spirit and scope of the invention, which is defined in the appended claims.

The invention claimed is:

1. A surgical instrument, comprising:
a chassis;
an outer tube comprising an outer tube proximal portion and an outer tube distal portion;
an inner tube extending within the outer tube and comprising an inner tube proximal portion and an inner tube distal portion;
a cantilever portion extending distally from the inner tube distal portion; and
one or more force sensors coupled to the cantilever portion;
wherein a center axis is defined through the outer tube proximal portion and the outer tube distal portion;
wherein the outer tube proximal portion is coupled to the chassis such that the outer tube is moveable along the center axis with reference to the chassis between a proximally retracted position and a distally extended position;
wherein the inner tube proximal portion is coupled to the chassis such that the inner tube is movable along the center axis with reference to the chassis and to the outer tube;
wherein the outer tube surrounds at least a first length of the cantilever portion in the distally extended position of the outer tube; and
wherein the outer tube surrounds less than the first length of the cantilever portion in the proximally retracted position of the outer tube.

2. The surgical instrument of claim 1, wherein:
the outer tube is configured to be locked in the proximally retracted position.

3. The surgical instrument of claim 1, wherein:
the outer tube is configured to be locked in the distally extended position.

4. The surgical instrument of claim 1, wherein:
the inner tube is configured to move along the center axis without constraint.

5. The surgical instrument of claim 1, wherein:
the surgical instrument further comprises a handle coupled to the chassis;
the outer tube extends along the center axis within the handle; and
the handle is configured to lock the outer tube in at least one of the proximally retracted position and the distally extended position.

6. The surgical instrument of claim 5, wherein:
the outer tube includes a first locking feature;
the handle includes a second locking feature; and
the first and second locking features are configured to be interlockable when the outer tube is in the distally extended position.

7. The surgical instrument of claim 5, wherein:
the handle comprises a distal stopper and a proximal stopper;
an interior channel is defined in the handle;
the outer tube comprises an outer surface and a post on the outer surface;
the post slides within the interior channel when the outer tube moves between the proximally retracted position and the distally extended position;
when the outer tube is in the proximally retracted position, the proximal stopper at least in part limits movement of the post in a distal direction; and
when the outer tube is in the distally extended position, the distal stopper at least in part limits movement of the post in a proximal direction.

8. The surgical instrument of claim 7, wherein:
the handle further comprises a rotatable rod and a button operatively coupled to the rotatable rod;
the distal stopper is on a distal end of the rotatable rod, and the proximal stopper is on a proximal end of the rotatable rod;
the button is configured to rotate the rotatable rod such that the proximal stopper and the distal stopper are moved into and out of the interior channel, the proximal stopper and the distal stopper being within the interior channel when the proximal stopper at least in part limits movement of the post in the distal direction and when the distal stopper at least in part limits movement of the post in the proximal direction.

9. The surgical instrument of claim 8, wherein:
the surgical instrument comprises one or more springs;
at least one spring of the one or more springs is coupled to the button and biases the button in an upward position; and
when the button is in the upward position, the proximal stopper and the distal stopper are within the interior channel.

10. The surgical instrument of claim 9, wherein:
when the button is depressed against the one or more springs, the distal stopper and the proximal stopper are moved outside of the interior channel.

11. The surgical instrument of claim 1, wherein:
the outer tube comprises an inner surface;
the inner tube extends within the outer tube and comprises an outer surface; and
the surgical instrument comprises a slip interface bushing between the outer surface of the inner tube and the inner surface of the outer tube.

12. The surgical instrument of claim 11, wherein:
the slip interface bushing is fixedly coupled to the outer surface of the inner tube and slidably contacts the inner surface of the outer tube.

13. The surgical instrument of claim 11, wherein:
the slip interface bushing comprises an inner perimeter and an outer perimeter;
the inner perimeter is fixedly coupled to the outer surface of the inner tube; and
the outer perimeter defines a slip interface in slidable contact with the inner surface of the outer tube.

14. The surgical instrument of claim 11, wherein:
the slip interface bushing comprises a bushing inner surface and a bushing outer surface;
the bushing inner surface is fixedly coupled to the outer surface of the inner tube; and
the bushing outer surface is chamfered and defines a slip interface with the inner surface of the outer tube.

15. The surgical instrument of claim 11, wherein:
the slip interface bushing is a first slip interface bushing and is between the outer surface of the inner tube and the inner surface of the outer tube at the inner tube distal portion; and
the surgical instrument further comprises a second slip interface bushing between the outer surface of the inner tube and the inner surface of the outer tube at the inner tube proximal portion.

16. The surgical instrument of claim 11, wherein:
the slip interface bushing maintains the outer surface of the inner tube spaced apart from the inner surface of the outer tube as the outer tube moves with reference to the inner tube and as the inner tube moves with reference to the outer tube.

17. The surgical instrument of claim 1, wherein:
the outer tube is slidably coupled to the chassis via a handle that defines a proximal limit of travel of the outer tube with reference to the chassis and a distal limit of travel of the outer tube with reference to the chassis.

18. The surgical instrument of claim 1, wherein:
the surgical instrument further comprises a coupler coupling the inner tube proximal portion to the chassis;
the inner tube has an inner tube center axis; and
the coupler includes a contact portion coupled to move in relation to the chassis in response to movement of the inner tube along the inner tube center axis.

19. The surgical instrument of claim 18, wherein:
the coupler includes a four-bar linkage operatively coupling the inner tube to the chassis.

20. The surgical instrument of claim 18, wherein:
the force sensor is a first force sensor;
the surgical instrument further comprises a second force sensor; and
the coupler is operably coupled to impart a force to the second force sensor in response to movement of the contact portion in relation to the chassis.

* * * * *